United States Patent [19]

Kurome et al.

[11] Patent Number: 5,824,503

[45] Date of Patent: Oct. 20, 1998

[54] GENE ENCODING ENDOGLYCOCERAMIDASE ACTIVATOR

[75] Inventors: Yoko Kurome; Hiroyuki Izu, both of Kusatsu; Yoshiya Izumi, Onojyo; Mutsumi Sano, Otsu; Ikunoshin Kato, Uji; Makoto Ito, Fukuoka, all of Japan

[73] Assignee: Takara Shuzo Co, Ltd., Kyoto-fu, Japan

[21] Appl. No.: 672,564

[22] Filed: Jun. 28, 1996

[30] Foreign Application Priority Data

Jun. 29, 1995 [JP] Japan .................................. 7-188466

[51] Int. Cl.$^6$ .................................................. C12N 15/00
[52] U.S. Cl. ................ 435/69.1; 435/252.3; 435/254.11; 435/254.2; 536/23.1; 536/24.33; 536/24.32; 530/350
[58] Field of Search ................ 536/23.1, 24.32, 536/24.33; 435/320.1, 240.2, 252.3, 254.11, 240.4, 254.2, 69.1; 530/350

[56] References Cited

U.S. PATENT DOCUMENTS 5,384,249   1/1995   Sasaki et al. ........................... 435/68.1
5,494,790   2/1996   Sasaki et al. ............................. 435/6

OTHER PUBLICATIONS

Makoto Ito et al., The Journal of Biological Chemistry, A Novel Glycosphingolipid degrading . . ., vol. 261, pp. 14278–14282 (1986).

Makoto Ito et al., The Journal of Biological Chemistry, Purification and Characterization . . ., vol. 264, pp. 9510–9519 (1989).

Su–Chen Li et al., Biochemical and Biophysical Research Communications, A Unique . . ., vol. 141, pp. 346–352 (1986).

Makoto Ito et al., The Journal of Biological Chemistry, Activator Proteins . . ., vol. 266, pp. 7919–7926 (1991).

Makoto Ito et al., The Journal of Biochemistry, Conversion of Endoglycoceramidase–Activator . . ., vol. 110, pp. 328–332 (1991).

*Primary Examiner*—Robert A. Wax
*Assistant Examiner*—Enrique D. Longton
*Attorney, Agent, or Firm*—Birch, Stewart, Kolasch & Birch, LLP

[57] ABSTRACT

An isolated DNA having a sequence encoding a polypeptide possessing endoglycoceramidase activator activity or functionally equivalent variants thereof; and a method for producing a polypeptide possessing endoglycoceramidase activator activity or functionally equivalent variants thereof by gene recombinant technology.

9 Claims, 6 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 580
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

| Met | Ser | Ser | Lys | Leu | Tyr | Arg | Tyr | Leu | Ala | Pro | Val | Ala | Val | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Ala | Thr | Val | Val | Ala | Gly | Ala | Gly | Val | Leu | Gly | Val | Gly | Ala | Ala |
|     |     |     |     | 20  |     |     |     |     | 25  |     |     |     |     | 30  |
| Ser | Ala | Ala | Thr | Thr | Ile | Thr | Pro | Phe | Asn | Asn | Ala | Cys | Gln | Ala |
|     |     |     |     | 35  |     |     |     |     | 40  |     |     |     |     | 45  |
| Thr | Pro | Ser | Ser | Ser | Leu | Ala | Gly | Gly | Pro | Gln | Thr | Gln | Val | Gln |
|     |     |     |     | 50  |     |     |     |     | 55  |     |     |     |     | 60  |
| Ala | Ala | Ser | Val | Thr | Val | Asp | Ala | Pro | Glu | Thr | Val | Ala | Pro | Gly |
|     |     |     |     | 65  |     |     |     |     | 70  |     |     |     |     | 75  |
| Glu | Glu | Phe | Val | Val | Thr | Ile | Ser | Pro | Pro | Pro | Ile | Ser | Val | Pro |
|     |     |     |     | 80  |     |     |     |     | 85  |     |     |     |     | 90  |
| Asn | Asp | Leu | Gly | Ser | Gly | Ala | Ser | Leu | Ser | Asn | Ile | Ser | Arg | Leu |
|     |     |     |     | 95  |     |     |     |     | 100 |     |     |     |     | 105 |
| Lys | Ile | Asp | Val | Ala | Met | Pro | Glu | Asn | Ala | Gln | Phe | Ile | Gly | Ala |
|     |     |     |     | 110 |     |     |     |     | 115 |     |     |     |     | 120 |
| Glu | Val | Val | Ala | Gly | Thr | Ser | Ala | Gly | Ile | Thr | Gly | Val | Ala | Pro |
|     |     |     |     | 125 |     |     |     |     | 130 |     |     |     |     | 135 |
| Asn | Val | Ile | Val | Val | Asn | Glu | Ser | Gly | Ser | Pro | Asp | Ala | Asn | Gly |
|     |     |     |     | 140 |     |     |     |     | 145 |     |     |     |     | 150 |
| Ser | Ile | Ile | Arg | Leu | Ser | Gly | Asn | Asn | Glu | Thr | Ile | Gly | Asn | Gly |
|     |     |     |     | 155 |     |     |     |     | 160 |     |     |     |     | 165 |
| Pro | Lys | Ser | Ser | Lys | Ser | Ser | Glu | Gly | Gly | Ile | Lys | Ala | Asn | Ala |
|     |     |     |     | 170 |     |     |     |     | 175 |     |     |     |     | 180 |
| Ser | Gly | Ser | Thr | Thr | Ser | Phe | Gln | Leu | Pro | Gln | Val | Lys | Ala | Thr |
|     |     |     |     | 185 |     |     |     |     | 190 |     |     |     |     | 195 |
| Leu | Lys | Ala | Gly | Ala | Ala | Gly | Glu | Ile | Ser | Met | Lys | Leu | Arg | Thr |
|     |     |     |     | 200 |     |     |     |     | 205 |     |     |     |     | 210 |
| Ala | Gly | Asn | Ala | Gly | Gln | Phe | Gly | Asn | Asp | Ala | Asn | Phe | Leu | Thr |
|     |     |     |     | 215 |     |     |     |     | 220 |     |     |     |     | 225 |
| Phe | Leu | Pro | Arg | Ala | Ser | Ala | Pro | Ile | Val | Gly | Thr | Val | Trp | Ala |
|     |     |     |     | 230 |     |     |     |     | 235 |     |     |     |     | 240 |
| Pro | Thr | Gln | Cys | Ser | Pro | Arg | Asp | Thr | Ala | Ala | Gly | Pro | Leu | Asn |
|     |     |     |     | 245 |     |     |     |     | 250 |     |     |     |     | 255 |
| Ala | Gly | Ala | Gly | Pro | Leu | Ala | Thr | Ile | Gln | Ile | Leu | Arg | Gln | Ala |
|     |     |     |     | 260 |     |     |     |     | 265 |     |     |     |     | 270 |
| Val | Ala | Thr | Val | Ser | Tyr | Leu | Asp | Gly | Pro | Ser | Ala | Val | Thr | Asn |
|     |     |     |     | 275 |     |     |     |     | 280 |     |     |     |     | 285 |
| Gly | Gly | Glu | Phe | Thr | Leu | Asn | Ala | Thr | Val | Val | Pro | Thr | Pro | Asp |
|     |     |     |     | 290 |     |     |     |     | 295 |     |     |     |     | 300 |

| | | | | | | | | | | | | | | |
|---|---|---|---|---|---|---|---|---|---|---|---|---|---|---|
|Ser|Gly|Gln|Val|Gln<br>305|Phe|Thr|Arg|Asp|Gly<br>310|Glu|Asp|Val|Gly|Ala<br>315|
|Pro|Val|Asp|Leu|Val<br>320|Asn|Gly|Lys|Ala|Ser<br>325|Leu|Thr|Gln|Ser|Leu<br>330|
|Asp|Thr|Asp|Gly|Asp<br>335|Tyr|Ala|Tyr|Glu|Ala<br>340|Lys|Phe|Leu|Gly|Ala<br>345|
|Glu|Phe|Phe|Asn|Pro<br>350|Ser|Ser|Ala|Ala|Lys<br>355|Thr|Val|Thr|Val|Thr<br>360|
|Ser|Gln|Asp|Ile|Gln<br>365|Thr|Thr|Thr|Ser|Val<br>370|Thr|Gly|Pro|Asp|His<br>375|
|Asp|Ala|Tyr|Arg|Asp<br>380|Gln|Pro|Val|Asn|Leu<br>385|Thr|Ala|Lys|Val|Glu<br>390|
|Pro|Gly|Val|Ser|Gly<br>395|Gly|Thr|Val|Ala|Phe<br>400|Glu|Val|Asp|Gly|Thr<br>405|
|Pro|Val|Gly|Thr|Ala<br>410|Asp|Val|Met|Asp|Asp<br>415|Gly|Ala|Ala|Val|Leu<br>420|
|Pro|His|Thr|Phe|Thr<br>425|Thr|Asn|Gly|Thr|His<br>430|Arg|Val|Ile|Ala|Arg<br>435|
|Tyr|Ser|Gly|Ala|Glu<br>440|Gly|Ile|Ser|Pro|Ser<br>445|Val|Ser|Leu|Gln|Tyr<br>450|
|Pro|Val|Ser|Val|Thr<br>455|Glu|Ala|Pro|Ala|Ala<br>460|Asp|Val|Ala|Thr|Thr<br>465|
|Ile|Thr|Val|Asp|Pro<br>470|Ile|Ala|Ser|Thr|Ala<br>475|Lys|Gly|Ser|Pro|Val<br>480|
|Thr|Leu|Thr|Ala|Arg<br>485|Leu|Asp|Pro|Ala|Asp<br>490|Ala|Arg|Gly|Thr|Val<br>495|
|Gln|Phe|Lys|Leu|Gly<br>500|Asp|Val|Leu|Leu|Gly<br>505|Gly|Pro|Val|Arg|Val<br>510|
|Asp|Ala|Asn|Gly|Val<br>515|Ala|Thr|Leu|Thr|Thr<br>520|Phe|Phe|Gln|Asn|Pro<br>525|
|Gly|Glu|Phe|Val|Val<br>530|Thr|Ala|Gln|Phe|Thr<br>535|Ala|Asp|Ala|Gly|Phe<br>540|
|Ile|Asp|Ser|Ala|Ala<br>545|Ser|Pro|Val|Asn|Leu<br>550|Thr|Val|Thr|Gly|Asp<br>555|
|Pro|Asp|Thr|Ile|Pro<br>560|Asn|Pro|Glu|Gly|Gly<br>565|Gly|Ser|Leu|Ala|Gly<br>570|
|Leu|Ser|Gly|Leu|Phe<br>575|Gly|Ser|Leu|Gly|Gly<br>580| | | | | |

(2) INFORMATION FOR SEQ ID NO:2:

(i) SEQUENCE CHARACTERISTICS:
        (A) LENGTH: 1740 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:2:

```
ATGAGTTCCA AGCTGTACCG CTACCTCGCG CCGGTCGCCG TGGGCGCGAC GGTGGTCGCC      60
GGTGCCGGAG TTCTGGGTGT GGGGGCCGCT TCCGCGGCGA CGACGATCAC GCCGTTCAAC     120
AACGCATGTC AGGCGACGCC GTCGTCGAGC CTGGCCGGTG GGCCACAGAC TCAGGTGCAG     180
GCGGCGTCGG TGACGGTCGA CGCACCGGAG ACCGTCGCTC CCGGTGAGGA GTTCGTGGTG     240
ACGATCTCGC CGCCGCCGAT CTCGGTGCCC AACGATCTGG GTTCCGGCGC GAGCCTGTCG     300
```

```
AACATCTCGC  GGCTCAAGAT  CGACGTCGCG  ATGCCGGAGA  ACGCGCAGTT  CATCGGCGCC    360

GAGGTGGTGG  CCGGAACGTC  AGCGGGCATC  ACGGGTGTCG  CGCCCAACGT  CATCGTCGTC    420

AACGAGAGTG  GTAGTCCGGA  CGCGAACGGC  TCGATCATCC  GGCTGTCCGG  AAACAACGAG    480

ACGATCGGCA  ACGGACCGAA  GTCCTCGAAG  AGTTCCGAGG  GCGGTATCAA  GGCGAACGCG    540

TCGGGCAGCA  CCACGTCCTT  CCAGTTGCCG  CAGGTCAAGG  CCACCCTCAA  GGCGGGCGCG    600

GCCGGCGAGA  TCTCGATGAA  GCTGCGCACC  GCAGGAAACG  CCGGGCAGTT  CGGCAACGAC    660

GCGAACTTCC  TCACGTTCCT  GCCCCGCGCC  AGCGCACCGA  TCGTCGGCAC  GGTCTGGGCC    720

CCCACCCAGT  GCTCGCCGCG  TGACACCGCG  GCCGGCCCGC  TCAACGCGGG  AGCCGGTCCG    780

CTGGCCACGA  TCCAGATCCT  GCGGCAGGCG  GTCGCCACCG  TCAGCTACCT  GGACGGTCCG    840

AGCGCGGTGA  CCAACGGCGG  CGAGTTCACG  CTCAACGCCA  CGGTCGTGCC  CACCCCGGAC    900

AGCGGTCAGG  TCCAGTTCAC  CCGGGACGGT  GAGGACGTCG  GCGCGCCGGT  CGATCTGGTG    960

AACGGCAAGG  CGTCGCTGAC  GCAGTCGCTC  GACACCGACG  GCGACTACGC  CTACGAGGCG   1020

AAGTTCCTGG  GCGCGGAGTT  CTTCAATCCG  TCGTCCGCCG  CGAAGACGGT  CACGGTGACC   1080

TCGCAGGACA  TCCAGACCAC  CACGTCGGTC  ACCGGACCTG  ACCACGACGC  CTACCGCGAC   1140

CAGCCGGTGA  ACCTCACCGC  GAAGGTCGAG  CCGGGCGTCT  CGGGCGGCAC  GGTGGCTTTC   1200

GAGGTCGACG  GAACCCCGGT  CGGCACCGCC  GATGTGATGG  ATGACGGCGC  GGCGGTGCTC   1260

CCGCACACCT  TCACCACCAA  CGGCACGCAC  CGCGTGATCG  CCCGCTACTC  GGGTGCCGAG   1320

GGGATCTCCC  CGTCGGTCTC  GCTGCAGTAC  CCGGTCAGCG  TCACCGAGGC  GCCGGCCGCC   1380

GACGTGGCCA  CCACGATCAC  GGTCGATCCG  ATCGCGTCGA  CTGCCAAGGG  CTCGCCGGTG   1440

ACCCTCACCG  CGCGTCTCGA  TCCGGCCGAC  GCCCGGGGCA  CGGTGCAGTT  CAAGCTCGGC   1500

GACGTCCTGC  TCGGCGGACC  GGTGCGGGTG  GATGCGAACG  GTGTCGCGAC  ACTGACGACG   1560

TTCTTCCAGA  ACCCCGGCGA  GTTCGTCGTC  ACGGCCCAGT  TCACCGCCGA  CGCCGGTTTC   1620

ATCGACTCGG  CAGCGAGCCC  GGTTAACCTC  ACGGTGACCG  GTGATCCGGA  CACCATTCCG   1680

AATCCGGAGG  GCGGCGGAAG  CCTCGCAGGC  CTTTCGGGAC  TGTTCGGTAG  CTTGGGCGGC   1740
```

( 2 ) INFORMATION FOR SEQ ID NO:3:

( i ) SEQUENCE CHARACTERISTICS:
        ( A ) LENGTH: 237 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ser  Ala  Thr  Thr  Ile  Thr  Pro  Phe  Asn  Asn  Ala  Cys  Gln  Ala  Thr
 1                   5                        10                       15

Pro  Ser  Ser  Ser  Leu  Ala  Gly  Gly  Pro  Gln  Thr  Gln  Val  Gln  Ala
                    20                        25                       30

Ala  Ser  Val  Thr  Val  Asp  Ala  Pro  Glu  Thr  Val  Ala  Pro  Gly  Glu
                    35                        40                       45

Glu  Phe  Val  Val  Thr  Ile  Ser  Pro  Pro  Ile  Ser  Val  Pro  Asn
                    50                        55                       60

Asp  Leu  Gly  Ser  Gly  Ala  Ser  Leu  Ser  Asn  Ile  Ser  Arg  Leu  Lys
                    65                        70                       75

Ile  Asp  Val  Ala  Met  Pro  Glu  Asn  Ala  Gln  Phe  Ile  Gly  Ala  Glu
                    80                        85                       90

Val  Val  Ala  Gly  Thr  Ser  Ala  Gly  Ile  Thr  Gly  Val  Ala  Pro  Asn
```

|     |     |     |     | 9 5 |     |     |     |     | 1 0 0 |     |     |     |     | 1 0 5 |
| --- | --- | --- | --- | --- | --- | --- | --- | --- | --- | --- | --- | --- | --- | --- |
| Val | Ile | Val | Val | Asn<br>1 1 0 | Glu | Ser | Gly | Ser | Pro<br>1 1 5 | Asp | Ala | Asn | Gly | Ser<br>1 2 0 |
| Ile | Ile | Arg | Leu | Ser<br>1 2 5 | Gly | Asn | Asn | Glu | Thr<br>1 3 0 | Ile | Gly | Asn | Gly | Pro<br>1 3 5 |
| Lys | Ser | Ser | Lys | Ser<br>1 4 0 | Ser | Glu | Gly | Gly | Ile<br>1 4 5 | Lys | Ala | Asn | Ala | Ser<br>1 5 0 |
| Gly | Ser | Thr | Thr | Ser<br>1 5 5 | Phe | Gln | Leu | Pro | Gln<br>1 6 0 | Val | Lys | Ala | Thr | Leu<br>1 6 5 |
| Lys | Ala | Gly | Ala | Ala<br>1 7 0 | Gly | Glu | Ile | Ser | Met<br>1 7 5 | Lys | Leu | Arg | Thr | Ala<br>1 8 0 |
| Gly | Asn | Ala | Gly | Gln<br>1 8 5 | Phe | Gly | Asn | Asp | Ala<br>1 9 0 | Asn | Phe | Leu | Thr | Phe<br>1 9 5 |
| Leu | Pro | Arg | Ala | Ser<br>2 0 0 | Ala | Pro | Ile | Val | Gly<br>2 0 5 | Thr | Val | Trp | Ala | Pro<br>2 1 0 |
| Thr | Gln | Cys | Ser | Pro<br>2 1 5 | Arg | Asp | Thr | Ala | Ala<br>2 2 0 | Gly | Pro | Leu | Asn | Ala<br>2 2 5 |
| Gly | Ala | Gly | Pro | Leu<br>2 3 0 | Ala | Thr | Ile | Gln | Ile<br>2 3 5 | Leu | Arg |     |     |     |

( 2 ) INFORMATION FOR SEQ ID NO:4:

( i ) SEQUENCE CHARACTERISTICS:
        ( A ) LENGTH: 711 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:4:

| | | | | | |
|---|---|---|---|---|---|
| TCGGCGACGA | CGATCACGCC | GTTCAACAAC | GCATGTCAGG | CGACGCCGTC | GTCGAGCCTG | 6 0 |
| GCCGGTGGGC | CACAGACTCA | GGTGCAGGCG | GCGTCGGTGA | CGGTCGACGC | ACCGGAGACC | 1 2 0 |
| GTCGCTCCCG | GTGAGGAGTT | CGTGGTGACG | ATCTCGCCGC | CGCCGATCTC | GGTGCCCAAC | 1 8 0 |
| GATCTGGGTT | CCGGCGCGAG | CCTGTCGAAC | ATCTCGCGGC | TCAAGATCGA | CGTCGCGATG | 2 4 0 |
| CCGGAGAACG | CGCAGTTCAT | CGGCGCCGAG | GTGGTGGCCG | GAACGTCAGC | GGGCATCACG | 3 0 0 |
| GGTGTCGCGC | CCAACGTCAT | CGTCGTCAAC | GAGAGTGGTA | GTCCGGACGC | GAACGGCTCG | 3 6 0 |
| ATCATCCGGC | TGTCCGGAAA | CAACGAGACG | ATCGGCAACG | GACCGAAGTC | CTCGAAGAGT | 4 2 0 |
| TCCGAGGGCG | GTATCAAGGC | GAACGCGTCG | GGCAGCACCA | CGTCCTTCCA | GTTGCCGCAG | 4 8 0 |
| GTCAAGGCCA | CCCTCAAGGC | GGGCGCGGCC | GGCGAGATCT | CGATGAAGCT | GCGCACCGCA | 5 4 0 |
| GGAAACGCCG | GGCAGTTCGG | CAACGACGCG | AACTTCCTCA | CGTTCCTGCC | CCGCGCCAGC | 6 0 0 |
| GCACCGATCG | TCGGCACGGT | CTGGGCCCCC | ACCCAGTGCT | CGCCGCGTGA | CACCGCGGCC | 6 6 0 |
| GGCCCGCTCA | ACGCGGGAGC | CGGTCCGCTG | GCCACGATCC | AGATCCTGCG | G | 7 1 1 |

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal fragment ( x i ) SEQUENCE DESCRIPTION: SEQ ID NO:5:

```
Ala  Thr  Thr  Ile  Thr  Pro  Phe  Asn  Asn  Ala  Xaa  Gln  Ala  Thr  Pro
 1              5                        10                       15
Ser  Ser  Xaa  Leu  Ala  Gly  Gly  Pro  Gln  Thr
                20                       25
```

( 2 ) INFORMATION FOR SEQ ID NO:6:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal fragment ( x i ) SEQUENCE DESCRIPTION: SEQ ID NO:6:

```
Leu  Arg  Thr  Ala  Gly  Asn  Ala  Gly  Gln  Phe  Gly  Asn  Asp  Ala  Asn
 1              5                        10                       15
Phe  Leu  Thr  Phe  Leu  Pro  Arg  Ala  Ser
                20
```

( 2 ) INFORMATION FOR SEQ ID NO:7:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO:7:

```
GCCACCACCA  TCACSCCSTT  CAACAACGCV  CCSCAGGCSA  CCCC                    4 4
```

( 2 ) INFORMATION FOR SEQ ID NO:8:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO:8:

```
ACCGCCGGCA  ACGCVGGYCA  GTTCGGYAAC  GAYGCVAACT  TCCTSACCTT  CCTSCC      5 6
```

( 2 ) INFORMATION FOR SEQ ID NO:9:

( i ) SEQUENCE CHARACTERISTICS:
        ( A ) LENGTH: 417 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Ala  Thr  Thr  Ile  Thr  Pro  Phe  Asn  Asn  Ala  Cys  Gln  Ala  Thr  Pro
 1              5                        10                       15
Ser  Ser  Ser  Leu  Ala  Gly  Gly  Pro  Gln  Thr  Gln  Val  Gln  Ala  Ala
                20                       25                       30
Ser  Val  Thr  Val  Asp  Ala  Pro  Glu  Thr  Val  Ala  Pro  Gly  Glu  Glu
                35                       40                       45
```

```
Phe  Val  Val  Thr  Ile  Ser  Pro  Pro  Pro  Ile  Ser  Val  Pro  Asn  Asp
               50                       55                            60

Leu  Gly  Ser  Gly  Ala  Ser  Leu  Ser  Asn  Ile  Ser  Arg  Leu  Lys  Ile
               65                       70                            75

Asp  Val  Ala  Met  Pro  Glu  Asn  Ala  Gln  Phe  Ile  Gly  Ala  Glu  Val
               80                       85                            90

Val  Ala  Gly  Thr  Ser  Ala  Gly  Ile  Thr  Gly  Val  Ala  Pro  Asn  Val
               95                      100                           105

Ile  Val  Val  Asn  Glu  Ser  Gly  Ser  Pro  Asp  Ala  Asn  Gly  Ser  Ile
              110                      115                           120

Ile  Arg  Leu  Ser  Gly  Asn  Asn  Glu  Thr  Ile  Gly  Asn  Gly  Pro  Lys
              125                      130                           135

Ser  Ser  Lys  Ser  Ser  Glu  Gly  Gly  Ile  Lys  Ala  Asn  Ala  Ser  Gly
              140                      145                           150

Ser  Thr  Thr  Ser  Phe  Gln  Leu  Pro  Gln  Val  Lys  Ala  Thr  Leu  Lys
              155                      160                           165

Ala  Gly  Ala  Ala  Gly  Glu  Ile  Ser  Met  Lys  Leu  Arg  Thr  Ala  Gly
              170                      175                           180

Asn  Ala  Gly  Gln  Phe  Gly  Asn  Asp  Ala  Asn  Phe  Leu  Thr  Phe  Leu
              185                      190                           195

Pro  Arg  Ala  Ser  Ala  Pro  Ile  Val  Gly  Thr  Val  Trp  Ala  Pro  Thr
              200                      205                           210

Gln  Cys  Ser  Pro  Arg  Asp  Thr  Ala  Ala  Gly  Pro  Leu  Asn  Ala  Gly
              215                      220                           225

Ala  Gly  Pro  Leu  Ala  Thr  Ile  Gln  Ile  Leu  Arg  Gln  Ala  Val  Ala
              230                      235                           240

Thr  Val  Ser  Tyr  Leu  Asp  Gly  Pro  Ser  Ala  Val  Thr  Asn  Gly  Gly
              245                      250                           255

Glu  Phe  Thr  Leu  Asn  Ala  Thr  Val  Val  Pro  Thr  Pro  Asp  Ser  Gly
              260                      265                           270

Gln  Val  Gln  Phe  Thr  Arg  Asp  Gly  Glu  Asp  Val  Gly  Ala  Pro  Val
              275                      280                           285

Asp  Leu  Val  Asn  Gly  Lys  Ala  Ser  Leu  Thr  Gln  Ser  Leu  Asp  Thr
              290                      295                           300

Asp  Gly  Asp  Tyr  Ala  Tyr  Glu  Ala  Lys  Phe  Leu  Gly  Ala  Glu  Phe
              305                      310                           315

Phe  Asn  Pro  Ser  Ser  Ala  Ala  Lys  Thr  Val  Thr  Val  Thr  Ser  Gln
              320                      325                           330

Asp  Ile  Gln  Thr  Thr  Thr  Ser  Val  Thr  Gly  Pro  Asp  His  Asp  Ala
              335                      340                           345

Tyr  Arg  Asp  Gln  Pro  Val  Asn  Leu  Thr  Ala  Lys  Val  Glu  Pro  Gly
              350                      355                           360

Val  Ser  Gly  Gly  Thr  Val  Ala  Phe  Glu  Val  Asp  Gly  Thr  Pro  Val
              365                      370                           375

Gly  Thr  Ala  Asp  Val  Met  Asp  Asp  Gly  Ala  Ala  Val  Leu  Pro  His
              380                      385                           390

Thr  Phe  Thr  Thr  Asn  Gly  Thr  His  Arg  Val  Ile  Ala  Arg  Tyr  Ser
              395                      400                           405

Gly  Ala  Glu  Gly  Ile  Ser  Pro  Ser  Val  Ser  Leu  Gln
              410                      415
```

( 2 ) INFORMATION FOR SEQ ID NO:10:

( i ) SEQUENCE CHARACTERISTICS:
        ( A ) LENGTH: 1251 base pairs (B) TYPE: nucleic acid
(C) STRANDEDNESS: double
(D) TOPOLOGY: linear (i i) MOLECULE TYPE: genomic DNA (x i) SEQUENCE DESCRIPTION: SEQ ID NO:10:

| | | | | | | |
|---|---|---|---|---|---|---|
| GCGACGACGA | TCACGCCGTT | CAACAACGCA | TGTCAGGCGA | CGCCGTCGTC | GAGCCTGGCC | 60 |
| GGTGGGCCAC | AGACTCAGGT | GCAGGCGGCG | TCGGTGACGG | TCGACGCACC | GGAGACCGTC | 120 |
| GCTCCCGGTG | AGGAGTTCGT | GGTGACGATC | TCGCCGCCGC | CGATCTCGGT | GCCCAACGAT | 180 |
| CTGGGTTCCG | GCGCGAGCCT | GTCGAACATC | TCGCGGCTCA | AGATCGACGT | CGCGATGCCG | 240 |
| GAGAACGCGC | AGTTCATCGG | CGCCGAGGTG | GTGGCCGGAA | CGTCAGCGGG | CATCACGGGT | 300 |
| GTCGCGCCCA | ACGTCATCGT | CGTCAACGAG | AGTGGTAGTC | CGGACGCGAA | CGGCTCGATC | 360 |
| ATCCGGCTGT | CCGGAAACAA | CGAGACGATC | GGCAACGGAC | CGAAGTCCTC | GAAGAGTTCC | 420 |
| GAGGGCGGTA | TCAAGGCGAA | CGCGTCGGGC | AGCACCACGT | CCTTCCAGTT | GCCGCAGGTC | 480 |
| AAGGCCACCC | TCAAGGCGGG | CGCGGCCGGC | GAGATCTCGA | TGAAGCTGCG | CACCGCAGGA | 540 |
| AACGCCGGGC | AGTTCGGCAA | CGACGCGAAC | TTCCTCACGT | TCCTGCCCCG | CGCCAGCGCA | 600 |
| CCGATCGTCG | GCACGGTCTG | GGCCCCCACC | CAGTGCTCGC | CGCGTGACAC | CGCGGCCGGC | 660 |
| CCGCTCAACG | CGGGAGCCGG | TCCGCTGGCC | ACGATCCAGA | TCCTGCGGCA | GGCGGTCGCC | 720 |
| ACCGTCAGCT | ACCTGGACGG | TCCGAGCGCG | GTGACCAACG | GCGGCGAGTT | CACGCTCAAC | 780 |
| GCCACGGTCG | TGCCCACCCC | GGACAGCGGT | CAGGTCCAGT | TCACCCGGGA | CGGTGAGGAC | 840 |
| GTCGGCGCGC | CGGTCGATCT | GGTGAACGGC | AAGGCGTCGC | TGACGCAGTC | GCTCGACACC | 900 |
| GACGGCGACT | ACGCCTACGA | GGCGAAGTTC | CTGGGCGCGG | AGTTCTTCAA | TCCGTCGTCC | 960 |
| GCCGCGAAGA | CGGTCACGGT | GACCTCGCAG | GACATCCAGA | CCACCACGTC | GGTCACCGGA | 1020 |
| CCTGACCACG | ACGCCTACCG | CGACCAGCCG | GTGAACCTCA | CCGCGAAGGT | CGAGCCGGGC | 1080 |
| GTCTCGGGCG | GCACGGTGGC | TTTCGAGGTC | GACGGAACCC | CGGTCGGCAC | CGCCGATGTG | 1140 |
| ATGGATGACG | GCGCGGCGGT | GCTCCCGCAC | ACCTTCACCA | CCAACGGCAC | GCACCGCGTG | 1200 |
| ATCGCCCGCT | ACTCGGGTGC | CGAGGGGATC | TCCCCGTCGG | TCTCGCTGCA | G | 1251 |

(2) INFORMATION FOR SEQ ID NO:11:

(i) SEQUENCE CHARACTERISTICS:
(A) LENGTH: 14 base pairs
(B) TYPE: nucleic acid
(C) STRANDEDNESS: single
(D) TOPOLOGY: linear (i i) MOLECULE TYPE: other nucleic acid (synthetic DNA)

(x i) SEQUENCE DESCRIPTION: SEQ ID NO:11:

| | |
|---|---|
| TTAAGTTAAC TTAA | 14 |

GENE ENCODING ENDOGLYCOCERAMIDASE ACTIVATOR

BACKGROUND OF THE INVENTION

1. Field of the Invention

The present invention relates to a DNA encoding a polypeptide which activates endoglycoceramidase, an enzyme useful for structural, functional and other analyses of glycolipids in sugar chain engineering, or which possesses endoglycoceramidase activator activity. The present invention also relates to an industrial production method for a polypeptide possessing endoglycoceramidase activator activity using a recombinant incorporating a recombinant plasmid having the DNA inserted therein.

2. Discussion of the Related Art

Endoglycoceramidase (EC3.2.1.123), an enzyme first isolated from the Actinomycetes of Rhodococcus strain [The Journal of Biological Chemistry 261, 14278–14282 (1986)] hydrolyzes the glycoside linkage between the sugar chain and ceramide in glycosphingolipid to liberate the sugar chain and ceramide in their complete form. Rhodococcus strains are also known to produce three different types of endoglycoceramidase (I, II, III) of different substrate specificities [The Journal of Biological Chemistry 264 (16) 9510–9519 (1989)]. Other known types of endoglycoceramidase include leech-derived endoglycoceramidase (ceramide-glycanase)[Biochemical and Biophysical Research Communications 141, 346–352 (1986)]. Although these enzymes are capable of efficiently decomposing glycolipids in the presence of various surfactants, glycolipid decomposition by them in the absence of surfactants is very slow.

On the other hand, the endoglycoceramidase-producing Rhodococcus strain produce two proteinic activators (activator I, activator II) which activate endoglycoceramidase with molecular specificity to allow endoglycoceramidase to hydrolyze glycolipids even in the absence of surfactants, at the same time with the endoglycoceramidase production. Activator I activates endoglycoceramidase I, while activator II activates endoglycoceramidase II. It is a well-known fact, however, that activator II activates endoglycoceramidase II more potently than endoglycoceramidase I, although it activates endoglycoceramidase I as well, and that activator II is also capable of activating leech-derived endoglycoceramidase (ceramide-glycanase) [The Journal of Biological Chemistry 266 (12) 7919–7926 (1991)].

Also, activator II, which has a molecular weight of 69.2 kDa, has been shown to be digested to 27.9 kDa by complete digestion with trypsin, while retaining its activity in an intact state [The Journal of Biochemistry 110, 328–332 (1991)]. In the presence of activator II, the optimum pH for endoglycoceramidase II shifts toward the neutral side, making it possible for endoglycoceramidase II to hydrolyze glycolipids even at pH 7.5. These facts suggest that the use of activator II may permit endoglycoceramidase II to exert its action on viable cells under physiological conditions (nearly neutral pH, in the absence of surfactants) under which the action of the enzyme is otherwise hampered. In other words, the use of activator II has been proven to enable the analysis of intracellular function of glycolipids by use of endoglycoceramidase II.

It should be noted, however, that the action of endoglycoceramidase II on viable cells requires large amounts of high-purity endoglycoceramidase II and endoglycoceramidase activator II. Production of endoglycoceramidase activator II using the producer Rhodococcus requires long cultivation time and many steps of purification; it is very difficult to obtain large amounts of high-purity activator II. There is therefore need for a method of producing the enzyme at lower cost and higher purity.

Also, because the amino acid sequence and gene structure of endoglycoceramidase activator II remain unknown, it is difficult to produce endoglycoceramidase activator II by gene engineering technology.

Accordingly, an objective of the present invention is to provide a DNA encoding a polypeptide possessing endoglycoceramidase activator activity. Another objective of the present invention is to provide a method of producing an endoglycoceramidase activator by gene engineering technology.

SUMMARY OF THE INVENTION

In order to achieve the above object, the present inventors conducted intensive studies in an effort to isolate the DNA encoding a polypeptide possessing endoglycoceramidase activator activity for elucidation of its nucleotide sequence. As a result, the present inventors at last succeeded in isolating a DNA encoding a polypeptide possessing endoglycoceramidase activator activity, and in elucidating the nucleotide sequence of the gene structure involved in the activity. Also, they succeeded in expressing the DNA in an organism to which a plasmid vector carrying the DNA is introduced. Based upon these facts, the present invention has been completed.

In one embodiment, the present invention relates to an isolated DNA having a sequence encoding a polypeptide possessing endoglycoceramidase activator activity or functionally equivalent variants thereof. Specifically, the isolated DNA comprises a DNA sequence selected from the group consisting of (a) to (d):

(a) a DNA sequence of SEQ ID NO:2 or SEQ ID NO:4, or a fragment thereof;

(b) a DNA sequence encoding an amino acid sequence of SEQ ID NO:1 or SEQ ID NO:3, or a fragment thereof;

(c) a DNA sequence encoding an amino acid sequence resulting from deletion, addition, insertion or substitution of one or more amino acids in the amino acid sequence of SEQ ID NO:1 or SEQ ID NO:3, or a fragment thereof; and (d) a DNA sequence capable of hybridizing to any one of (a) to (c) above.

In another embodiment, the present invention relates to a recombinant DNA which comprises the isolated DNA of the present invention, to a vector comprising the recombinant DNA, and to a cell of a procaryote or eucaryote transformed with the vector.

In another embodiment, the present invention relates to a method for producing a polypeptide possessing endoglycoceramidase activator activity or functionally equivalent variants thereof, comprising the steps of:

(a) culturing the cell of the present invention; and (b) recovering the polypeptide possessing endoglycoceramidase activator activity or functionally equivalent variants thereof from the culture obtained in Step (a).

In another embodiment, the present invention relates to a polypeptide possessing endoglycoceramidase activator activity or functionally equivalent variants thereof produced by the present method or encoded by the isolated DNA of the present invention.

In another embodiment, the present invention relates to a synthetic oligonucleotide probe or primer which specifically hybridizes with the isolated DNA of the present invention.

In another embodiment, the present invention relates to an antibody or fragment thereof which specifically binds the polypeptide of the present invention.

The amino acid sequence involved in the activity of endoglycoceramidase activator and its nucleotide sequence have first been established by the present invention, thereby providing the gene of endoglycoceramidase activator and an industrially advantageous method for producing a polypeptide possessing endoglycoceramidase activator activity by gene engineering techniques.

By use of the DNA sequence encoding endoglycoceramidase activator of the present invention, it becomes possible to probe DNA which has a different sequence from the present invention but possibly encodes a polypeptide possessing a functionally equivalent activity to the present invention. Also, the amino acid sequence corresponding to the DNA sequence encoding endoglycoceramidase activator of the present invention is useful for the preparation of the antibody to the endoglycoceramidase activator of the present invention.

DETAILED DESCRIPTION OF THE INVENTION

Figure 1:
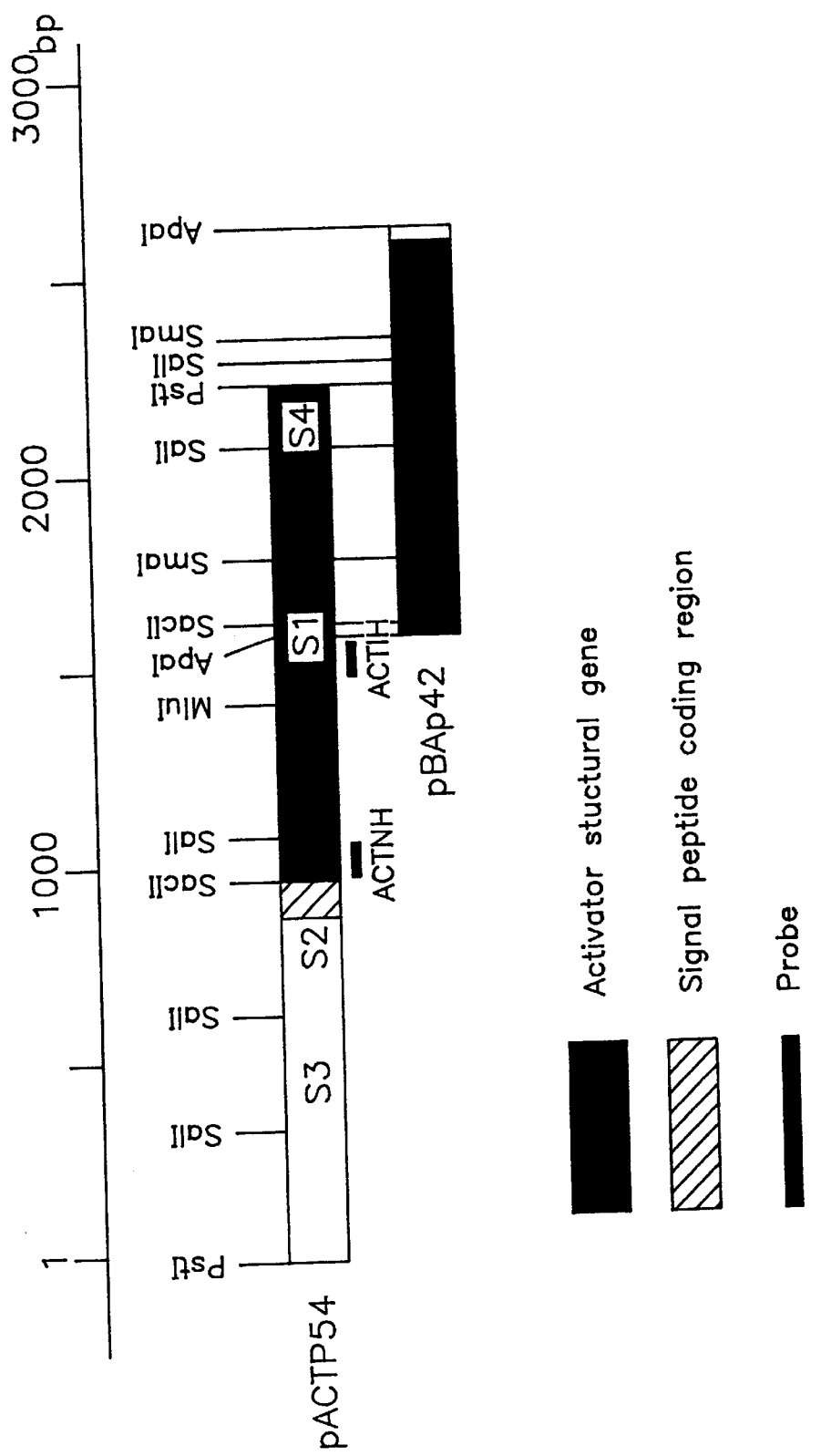
FIG. 1 shows schematic representations of the structural gene encoding endoglycoceramidase activator II, and the probe sequences of ACTHI and ACTNH.

Endoglycoceramidase activator as mentioned herein refers to a protein which activates endoglycoceramidase in the absence of surfactant.

Endoglycoceramidase activator activity as mentioned herein can be determined as follows:

The activity can be determined by the method described in The Journal of Biological Chemistry 266 (12) 7919–7926 (1991), using an extract from recombinant *Escherichia coli* cells. Specifically, 40 nmol of asialo-GM1, 5 µg of bovine serum albumin, 0.3 milliunits of purified endoglycoceramidase and an appropriate amount of a crude extract (endoglycoceramidase activator protein) are mixed in 40 µl of a 20 mmol sodium acetate buffer (pH 5.5), previously isotonized with 0.85% NaCl, to yield a standard test mixture. Enzyme activity is then determined by the method described in The Journal of Biological Chemistry 264, 9510–9519 (1989). After incubation at 37° C. for 60 minutes, the reaction is terminated by the addition of 250 µl of a carbonate-cyanide solution (pH 11); reducing activity is assessed by the method of Park and Johnson [The Journal of Biological Chemistry 181, 149–151 (1949)]. For control experiment, the substrate and crude extract (endoglycoceramidase activator protein), or the substrate and endoglycoceramidase, are separately incubated. The sum of the both control values is subtracted from the above actual sample value. One unit of endoglycoceramidase activator protein is defined as the amount of endoglycoceramidase activator protein which increases the hydrolysis of asialo-GM1 by 1 µmol per minute under the above-described standard experimental conditions.

The term "a polypeptide possessing endoglycoceramidase activator activity" as used in the present specification includes not only those having an amino acid sequence of native endoglycoceramidase activator but also its variants due to modification of amino acid sequence by, for example, deletion, substitution, insertion, or addition of amino acid(s), as long as they are capable of activating endoglycoceramidase. "Native endoglycoceramidase activator" used herein includes, but is not limited to, those produced by Rhodococcus strains. Also included are those derived from other microorganisms, such as other Actinomycetes, bacteria, yeasts, fungi, Ascomycetes, and Basidiomycetes, and those derived from plants, animals, insects, and other living things.

The term "functionally equivalent variant" as used herein is defined as follows:

A naturally-occurring protein can undergo amino acid deletion, insertion, addition, substitution and other variations in its amino acid sequence due to modifications, etc. of the protein itself in vivo or during purification, as well as those due to polymorphism and variation of the gene encoding it. It is a well-known fact that there are some such polypeptides which are substantially equivalent to variation-free proteins in terms of physiological and biological activity. A polypeptide which is structurally different from the corresponding protein but has no significant functional difference from the protein is referred to as a functionally equivalent variant.

The same applies to polypeptides prepared by artificially introducing such variations into the amino acid sequence of a protein. Although more diverse variants can be thus obtained, the resulting variants are construed as functionally equivalent variants, as long as their physiological activity is substantially equivalent to that of the original variation-free protein.

For example, the methionine residue at the N-terminus of a protein expressed in *Escherichia coli* is reportedly often removed by the action of methionine aminopeptidase, but some such expressed proteins have the methionine residue and others do not. However, the presence or absence of the methionine residue does not affect protein activity in most cases. It is also known that a polypeptide resulting from replacement of a particular cysteine residue with serine in the amino acid sequence of human interleukin 2 (IL-2) retains IL-2 activity [Science, 224, 1431 (1984)].

In addition, in producing a protein by gene engineering, the desired protein is often expressed as a fused protein. For example, the N-terminal peptide chain derived from another protein is added to the N-terminus of the desired protein to enhance the expression of the desired protein, or purification of the desired protein is facilitated by adding an appropriate peptide chain to the N- or C-terminus of the desired protein, expressing the protein, and using a carrier showing affinity for the peptide chain added.

Also, with regards to the codon (triplet base combination) determining a particular amino acid on the gene, 1 to 6 kinds are known to exist for each amino acid. Therefore, there can be a large number of genes encoding an amino acid sequence, though depending on the amino acid sequence. In nature, the gene is not stable, commonly undergoing nucleic acid variation. A variation on the gene may not affect the amino acid sequence to be encoded (silent variation); in this case, it can be said that a different gene encoding the same amino acid sequence has been produced. The possibility is therefore unnegligible that even when a gene encoding a particular amino acid sequence is isolated, a variety of genes encoding the same amino acid sequence are produced with generation passage of the organism containing it.

Moreover, it is not difficult to artificially produce a variety of genes encoding the same amino acid sequence by means of various gene engineering techniques.

For example, when a codon used in the natural gene encoding the desired protein is low in availability in the host used to produce the protein by gene engineering, the amount of protein expressed is sometimes insufficient. In this case, expression of the desired protein is enhanced by artificially converting the codon into another one of high availability in the host without changing the amino acid sequence encoded. It is of course possible to artificially produce a variety of genes encoding a particular amino acid sequence. Such artificially produced different polynucleotides are therefore included in the scope of the present invention, as long as an amino acid sequence disclosed herein is encoded.

Additionally, a polypeptide resulting from at least one change, such as deletion, addition, insertion or substitution, of one or more amino acid residues in the amino acid sequence of the desired protein commonly possesses an activity functionally equivalent to that of the desired protein; genes encoding such polypeptides are also included in the scope of the present invention, whether isolated from natural sources or produced artificially.

In general, functionally equivalent variants are often homologous to each other in terms of genes encoding them. Nucleic acid molecules capable of hybridizing to a gene of the present invention, and encoding a polypeptide possessing endoglycoceramidase activator activity, are therefore also included in the scope of the present invention.

The present invention is hereinafter described in detail as to isolation and sequencing of the DNA of the present invention with reference to endoglycoceramidase activator II.

First, information regarding a partial amino acid sequence of purified endoglycoceramidase activator II is obtained. Specifically, endoglycoceramidase activator II as purified by the method described in The Journal of Biochemistry 110, 328–332 (1991), for instance, is directly subjected to the Edman degradation method [The Journal of Biological Chemistry 256, 7990–7997 (1981)] for amino acid sequencing by a conventional method. Alternatively, said activator may be partially hydrolyzed by the action of a protein hydrolase of high specificity, the resulting peptide fragment may be separated, purified and subjected to amino acid sequencing to determine its internal partial amino acid sequence.

On the basis of the thus-obtained partial amino acid sequence information, the endoglycoceramidase activator II gene is cloned. For this purpose, a commonly used PCR or hybridization method can be used.

Next, on the basis of the partial amino acid sequence information, synthetic oligonucleotides are designed for use as Southern hybridization probes. Separately, the genomic DNA of Rhodococcus sp. M-777 is completely digested with the appropriate restriction enzymes including MluI, SalI, PstI, and BamHI and subjected to agarose gel electrophoresis for separation [Molecular Cloning, A Laboratory Manual, 2nd ed., T. Maniatis et al., Chapter 6, 3–20, Cold Spring Harbor Laboratory Press, (1989)], and the separated fragments are blotted onto a nylon membrane by a conventional method [Molecular Cloning, A Laboratory Manual, 2nd ed., T. Maniatis et al., Chapter 9, 34, Cold Spring Harbor Laboratory Press, (1989)].

Hybridization can be conducted under commonly used conditions. For example, the nylon membrane is blocked at 65° C. in a prehybridization solution containing 6×SSC (1 ×SSC is prepared by dissolving 8.77 g NaCl and 4.41 g sodium citrate in 1 L of water), 0.5% SDS, 5 × Denhardt's solution and 100 $\mu$g/ml salmon sperm DNA, and each $^{32}$P-labeled synthetic oligonucleotide was added, followed by overnight incubation at 65° C. After the nylon membrane is washed in 2 × SSC containing 0.1% SDS at 55° C. for 30 minutes, an autoradiogram is taken to detect a DNA fragment that hybridizes to the synthetic oligonucleotide probe. After the DNA fragment corresponding to the band detected is extracted and purified from the gel, the DNA fragment is inserted into a plasmid vector by a commonly used method. Useful plasmid vectors include, but are not limited to, commercially available pUC18, pUC19, pUC119 and pTV118N (all are products of Takara Shuzo).

Then, thus-obtained recombinant plasmid is introduced into a host to transform the host. Usable host cells include procaryotic cells of bacteria (e.g., *Escherichia coli*) and Actinomyces, and eucaryotic cells of yeast, fungi, animals, plants, etc.

When the host is *Escherichia coli*, it may be of a wild strain or a variant strain, as long as it is capable of being transformed and expressing a gene. This plasmid introduction can be achieved by a commonly used method, such as the method described in Molecular Cloning, A Laboratory Manual 2nd. ed., T. Maniatis et al., Chapter 1, 74–84, Cold Spring Harbor Laboratory Press (1989).

Next, a transformant harboring the desired DNA fragment is selected. For this purpose, the characteristics of the plasmid vector are utilized. In the case of pUC19, for instance, colonies having a foreign gene introduced thereto are selected by selecting ampicillin-resistant colonies on an ampicillin-containing plate, or selecting ampicillin-resistant white colonies on a plate containing ampicillin, 5-bromo-4-chloro-3-indolyl- β-D-galactoside (X-Gal) and isopropyl-β-D-thiogalactopyranoside (IPTG).

Next, the colony having a vector containing the desired DNA fragment is then selected out of the above population. This selection is achieved by using colony hybridization [Molecular Cloning, A Laboratory Manual, 2nd ed., T. Maniatis et al., Chapter 1, 90–104, Cold Spring Harbor Laboratory Press (1989)] or plaque hybridization [Molecular Cloning, A Laboratory Manual, 2nd ed., T. Maniatis et al., Chapter 2, 108–117, Cold Spring Harbor Laboratory Press (1989)], chosen appropriately according to vector types. PCR methods [Molecular Cloning, A Laboratory Manual, 2nd ed., T. Maniatis et al., Chapter 14, 15–19, Cold Spring Harbor Laboratory Press (1989)] are also applicable.

Once the vector containing the obtained DNA fragment is selected, the base sequence of the obtained DNA fragment inserted in this vector is determined by an ordinary method, such as the dideoxy chain terminator method [Molecular Cloning, A Laboratory Manual, 2nd ed., T. Maniatis et al., Chapter 13, 3–10, Cold Spring Harbor Laboratory Press (1989)]. The thus-determined base sequence is compared with the N-terminal sequence, partial amino acid sequence, molecular weight, etc. of endoglycoceramidase activator II to know the gene structure and entire amino acid sequence of endoglycoceramidase activator II. When the obtained DNA fragment does not contain the full-length endoglycoceramidase activator II gene, the full-length endoglycoceramidase activator II gene can be obtained by digesting genomic DNA of Rhodococcus sp. M-777 with other restriction enzymes, obtaining the lacking portion from the digests by hybridization, etc. using a part of the DNA fragment obtained above as a probe, then joining the lacking portion.

The entire or part of the resulting endoglycoceramidase activator II gene as obtained above is inserted into an appropriate plasmid vector, which is then transformed into a host cell. The transformant thus obtained is cultured under commonly used conditions to produce a polypeptide possessing endoglycoceramidase activator II activity.

For example, when *Escherichia coli* and pET23b [produced by Novagen] are used as a host cell and plasmid vector, respectively, said transformant is cultured at 37° C. overnight in an L medium (0.1% Trypton, 0.05% yeast extract, 0.1% NaCl, pH 7.2) containing 100 µg/ml ampicillin; upon reach of an absorbance at 600 nm of about 0.5, IPTG is added, followed by further overnight shaking culture at 37° C. After completion of the cultivation, cells are recovered, disrupted by ultrasonication etc. and centrifuged. The resulting supernatant is subjected to an ordinary protein purification process as described below to yield high-purity endoglycoceramidase activator II. There may be the case where the polypeptide expressed can be produced in the form of inclusion body.

The expression of the gene product can be confirmed by, for example, determining endoglycoceramidase activator II activity. When the recombinant is *Escherichia coli*, for example, activity can be determined by the method described in the Journal of Biological Chemistry, 266 (12) 7919–7929 (1991), using the extract of the recombinant *Escherichia coli* as an enzyme solution. Specifically, since endoglycoceramidase II requires a surfactant, such as Triton X-100, for expression of its activity, endoglycoceramidase activator II activity can be assessed by measuring the increment of endoglycoceramidase II activity in the absence of surfactants caused by the addition of a crude extract.

Specifically, 40 nmol asialo-GM1 (produced by IATRON), 5 µg of bovine serum albumin, 0.3 milliunits of purified endoglycoceramidase II and an appropriate amount of the crude extract (endoglycoceramidase activator II protein) are mixed in 40 µl of a 20 mmol sodium acetate buffer (pH 5.5), previously isotonized with 0.85% NaCl, to yield a standard test mixture. Enzyme activity is then determined by the method described in The Journal of Biological Chemistry 264, 9510–9519 (1989). After incubation at 37° C. for 60 minutes, the reaction is terminated by the addition of 250 µl of a carbonate-cyanide solution (pH 11); reducing activity is assessed by the method of Park and Johnson [The Journal of Biological Chemistry 181, 149–151 (1949)]. For control experiment, the substrate and crude extract (endoglycoceramidase activator II protein), or the substrate and endoglycoceramidase, are separately incubated. The sum of the both control values is subtracted from the above actual sample value. One unit of endoglycoceramidase activator II protein is defined as the amount of said protein which increases the hydrolysis of asialo-GM1 by 1 µmol per minute under the above-described standard experimental conditions.

Expression can also be confirmed immunologically using an antiserum obtained by immunizing a rat with purified endoglycoceramidase activator II.

When the desired expression of endoglycoceramidase activator II is noted, optimum conditions for endoglycoceramidase activator II expression are selected.

Endoglycoceramidase activator II can be purified from the transformant culture by an ordinary method. That is, the transformant cells are collected by centrifugation, disrupted by ultrasonication, or the like, and then subjected to centrifugation, etc. to yield a cell-free extract, which can be purified by common protein purification methods, such as salting-out and various chromatographies including ion exchange, gel filtration, hydrophobic interaction and affinity chromatographies. Depending on the host-vector system used, the expression product is extracellularly secreted by the transformant; in this case, the product can be purified from the culture supernatant in the same manner as that described above. When the host is *Escherichia coli*, the expression product is sometimes formed as an insoluble inclusion body. In this case, cells are collected by centrifugation after cultivation, disrupted by ultrasonication, or the like, then subjected to centrifugation, etc. to separate the insoluble fraction containing the inclusion body. After being washed, the inclusion bodies are solubilized with a commonly used protein solubilizer, such as detergent urea or guanidine hydrochloride, followed by purification by various chromatographies, such as ion exchange, gel filtration, hydrophobic interaction and affinity chromatographies, as necessary, after which a refolding treatment by dialysis or dilution is conducted to yield a preparation of endoglycoceramidase activator II retaining its activity. This preparation may be purified by various chromatographies to yield a highly pure preparation of endoglycoceramidase activator II.

Using the endoglycoceramidase activator gene of the present invention, gene encoding the desired polypeptide possessing endoglycoceramidase activator activity or functionally equivalent variant thereof can be obtained from DNAs or cDNAs of other gene sources than that mentioned above by means of hybridization. To obtain the desired gene encoding a polypeptide possessing endoglycoceramidase activator activity or functionally equivalent variant thereof by hybridization, the following method, for example, can be used.

First, chromosomal DNA obtained from the desired gene source, or cDNA prepared from mRNA by means of reverse transcriptase, is joined to a plasmid or phage vector and introduced into a host to yield a library by a conventional method. The library is then cultured on a plate; the resulting colonies or plaques are transferred onto a nitrocellulose or nylon membrane and subjected to denaturing treatment to immobilize the DNA to the membrane. This membrane is incubated in a solution containing a probe labeled with $^{32}$P or the like (the probe used may be any gene encoding the amino acid sequence shown in SEQ ID NO:1 or SEQ ID NO:3, or a portion thereof; for example, the genes shown in SEQ ID NO:2 or SEQ ID NO:4, or a portion thereof can be used), to form a hybrid between the DNA on the membrane and the probe. For example, the membrane with DNA immobilized thereon is subjected to hybridization with the probe in a solution containing 6 × SSC, 1% sodium lauryl sulfate, 100 µg/ml salmon sperm DNA and 5 × Denhardt's solution (containing bovine serum albumin, polyvinylpyrrolidone and Ficoll, each at 0.1%) at 65° C. for 20 hours. After hybridization, the nonspecifically adsorbed portion is washed out, followed by autoradiography, etc. to identify clones that formed a hybrid with the probe. This procedure is repeated until only a single clone has formed the hybrid. The clone thus obtained has a gene encoding the desired protein inserted therein.

The nucleotide sequence of the gene obtained is then determined by, for example, the following method, to confirm if the gene obtained is identical with the desired gene encoding a polypeptide possessing endoglycoceramidase activator activity or functionally equivalent variant thereof.

When the recombinant is *Escherichia coli*, nucleotide sequencing for a clone obtained by hybridization can be achieved by culturing the *Escherichia coli* in a test tube, or the like, extracting the plasmid by a conventional method, digesting the extracted plasmid with restriction enzymes, separating the insert and subcloning it into M13 phage vector, or the like, and determining the nucleotide sequence by the dideoxy method. When the recombinant is a phage, basically the same procedure as that used above can be used to determine the nucleotide sequence. Basic experimental techniques for from cultivation to nucleotide sequencing are described in, for example, Molecular Cloning, A Laboratory Manual, 2nd ed., T. Maniatis et al., Cold Spring Harbor Laboratory Press (1989).

To confirm the identity of the gene obtained as the desired gene encoding a polypeptide possessing endoglycoceramidase activator activity or functionally equivalent variant thereof, the nucleotide sequence determined is compared with the nucleotide sequence of the endoglycoceramidase activator gene of the present invention and the amino acid sequence shown in SEQ ID NO:1 or SEQ ID NO:3 in the sequence listing.

If the gene obtained does not contain the entire region encoding a polypeptide possessing endoglycoceramidase activator activity or functionally equivalent variant thereof, the nucleotide sequence of the entire region encoding a polypeptide possessing endoglycoceramidase activator activity or functionally equivalent variant thereof that hybridizes to the endoglycoceramidase activator gene of the present invention can be determined by preparing a synthetic DNA primer from the gene obtained, and amplifying the lacking region by PCR or by screening the DNA library or cDNA library using the gene fragment obtained as a probe.

A polypeptide possessing endoglycoceramidase activator activity or functionally equivalent variant thereof can be obtained by gene engineering technology as follows: First, the obtained endoglycoceramidase activator gene or another gene encoding a polypeptide possessing functionally equivalent activity is joined to an expression vector which is capable of expressing the gene in an appropriate host cell, such as *Escherichia coli, Bacillus subtilis,* actinomyces, yeast, fungi, animal cell, insect cell or plant cell, by a conventional method, followed by introduction into the host cell, to yield a recombinant. By culturing this recombinant, a polypeptide possessing endoglycoceramidase activator activity can be produced. Also, by the use of a cell incapable of sugar chain biosynthesis as a host, e.g., a prokaryotic organism, such as *Escherichia coli* and *Bacillus subtilis,* actinomyces, or by the use of a variant yeast, fungi, animal, insect or plant cell which has lost its capability of sugar chain biosynthesis, an endoglycoceramidase activator polypeptide having no sugar chains can be expressed.

In some expression systems, the obtained endoglycoceramidase activator gene or a gene encoding functionally equivalent variant of endoglycoceramidase activator includes a region encoding a signal peptide for cellular secretion, resulting in extracellular secretion and accumulation of the desired polypeptide in the culture broth. In this case, the desired polypeptide can be recovered from the culture broth. When the desired polypeptide is accumulated in the recombinant, it may be recovered from cultured cells via cell disruption. In addition, when the polypeptide expressed in the recombinant is accumulated in the form of an insoluble substance (inclusion body), it may be recovered, then solubilized under mild conditions, e.g., with urea, followed by denaturant removal, to restore the original activity. Expression can be confirmed by determining endoglycoceramidase activator activity as described above.

A polypeptide possessing endoglycoceramidase activator activity can be purified from a recombinant by ordinary chromatographic techniques. For example, when the desired polypeptide is secreted extracellularly from the recombinant, the culture supernatant is subjected to a chromatography, such as hydrophobic interaction, ion exchange or gel filtration chromatography, to obtain the desired polypeptide as expressed. When the desired polypeptide is accumulated in the recombinant, cultured cells are disrupted and, if the desired polypeptide is present in a solubilized form, the supernatant is subjected to a chromatography, such as hydrophobic interaction, ion exchange or gel filtration chromatography, to obtain the desired polypeptide as expressed. When the expression product is accumulated as an insoluble substance, cells are disrupted, after which the precipitate is recovered and solubilized with a denaturant, such as urea. The denaturant is then removed, followed by refolding and subsequent chromatographic treatment as described above, to obtain a polypeptide with desired activity.

The present invention provides the primary structure of endoglycoceramidase activator, and the gene structure thereof. The elucidation of the gene structure achieved in the present invention permits the production of a polypeptide possessing endoglycoceramidase activator activity by gene engineering. By the present method using gene engineering technology, a highly pure polypeptide preparation possessing endoglycoceramidase activator activity can be produced at low cost.

EXAMPLES

The following examples illustrate the present invention but are not intended to limit the invention in any manner.

Example 1.

Cloning of endoglycoceramidase activator II structural gene (1) Extraction and purification of genomic DNA Rhodococcus sp. M-777, an endoglycoceramidase activator II producer, was inoculated to 30 ml of a medium (pH 7.0) comprising 1.5% mycological peptone (produced by OXOID), 0.2% NaCl and 0.1% yeast extract, and subjected to shaking culture at 28° C. for 3 days. The culture broth was transferred to 900 ml of the same medium and subjected to shaking culture at 28° C. for 3 days. After completion of the cultivation, the culture broth was centrifuged; cells were collected and suspended in 4.5 ml of a buffer (50 mM Tris-HCl, 50 mM EDTA, pH 8.0), then frozen and thawed. To this cell suspension, 2.5 ml of a buffer (50 mM Tris-HCl, 50 mM EDTA, pH. 8.0) containing 4 mg/ml lysozyme was added, followed by incubation at 30° C. for 16 hours. To this mixture, 10 ml of an extracting buffer (50 mM Tris-HCl, 1% SDS, 0.4 mg/ml proteinase K, pH 7.5) was added, followed by incubation at 50° C. for 16 hours, after which 10 ml of another extracting buffer (50 mM Tris-HCl, 0.5% SDS, 0.2 mg/ml proteinase K, pH 7.5) was added, followed by incubation for 8 hours. After the incubation mixture was allowed to cool to room temperature, an equal volume of a phenol/chloroform solution, previously saturated with TE buffer (10 mM Tris-HCl, 1 mM EDTA, pH 8.0), was added, followed by gentle rotary shaking for 16 hours and subsequent centrifugation at 3,500 rpm for 30 minutes, after which the supernatant was recovered. This solution was dialyzed against a buffer (10 mM Tris-HCl, 5 mM EDTA, pH 8.0) at 4° C. to yield a genomic DNA solution.

(2) Partial amino acid sequencing of endoglycoceramidase activator II

The 27.9 kDa trypsin digest of endoglycoceramidase activator II was first purified by the method described in The Journal of Biochemistry 110, 328–332 (1991). The N-terminal sequence of the purified 27.9 kDa trypsin digest of endoglycoceramidase activator II was then determined by the Edman degradation method. As a result, the N-terminal amino acid sequence (SEQ ID NO:5) was determined and designated as ACTN.

The internal amino acid sequence was then determined as follows:

To a test tube containing 4 µl pyridine, 1 µl 4-vinylpyridine, 1 µl tributylphosphine and 5 µl distilled water, a smaller sample tube containing the purified sample was inserted; the outer tube was vacuum sealed, followed by heating at 100° C. for 5 minutes to pyridylethylate the cysteine residues in the sample in a gas phase.

A 1 nmol sample thus S-pyridylethylated was dissolved in 50 µl of a 20 mM Tris buffer (pH 9.0) containing 4 M urea; 8 pmol of lysylendopeptidase (produced by Pierce) was added, followed by digestion at 37° C. for 16 hours. Reverse-phase chromatography was then conducted on a density gradient from distilled water containing 0.065% trifluoroacetic acid (TFA) to acetonitrile containing 0.05% TFA through a µRPC C2/C18 SC2.1/10 column (produced by Pharmacia) using a SMART system (produced by Pharmacia), to purify the peptide fragment. The peptide fragment thus purified was analyzed by the Edman degradation method using a model 477 gas-phase peptide sequencer (produced by Applied Biosystems). As a result, the internal partial amino acid sequence (SEQ ID NO:6) was determined and designated as ACTI.

(3) Cloning of DNA fragment containing endoglycoceramidase activator II gene.

The genomic DNA prepared in Example 1 (1), 25 µg, was digested with restriction enzymes BamHI, PstI and SalI (all produced by Takara Shuzo), each 100 U, at 37° C. for 6 hours; after additional 100 U of each enzyme was added, the reaction was continued for 16 hours. This reaction mixture, in an amount equivalent to 5 µg of DNA, was subjected to 0.7% agarose gel electrophoresis, after which the DNA was transferred onto a nylon membrane (Hybond-N+, produced by Amersham) by the Southern blotting method (Idenshi Kenkyuhou II, pp. 218–221, published by Tokyo Kagaku Dojin). This filter was provided in duplicate.

The hybridization probes used were the oligonucleotides ACTNH (SEQ ID NO:7) and ACTIH (SEQ ID NO:8) designed and synthesized on the basis of the N-terminal amino acid sequence ACTN (SEQ ID NO:5) and internal partial amino acid sequence ACTI (SEQ ID NO:6) determined in Example 1 (2). These oligonucleotide sequences were designed on the basis of codons of high availability in the host as determined from the known base sequences encoding various proteins for the genus Rhodococcus.

These synthetic oligonucleotides, each 10 pmol, were labeled with $^{32}$P using the MEGARABEL™ (produced by Takara Shuzo).

Each of the pair of filters prepared above was subjected to prehybridization at 65° C. for 3 hours in a solution containing 6 ×SSC (1 × SSC is an aqueous solution of 8.77 g of NaCl and 4.41 g of sodium citrate in 1 l of water), 0.5% SDS, 100 µg/ml herring sperm DNA and 5 × Denhardt's (containing bovine serum albumin, polyvinylpyrrolidone and Ficoll, each at 0.1% concentration), after which each of the labeled probes was added to a concentration of 0.5 pmol/ml, followed by overnight hybridization at 55° C. Each filter was then washed in 6× SSC at room temperature for 10 minutes, in 2 × SSC and 0.1% SDS at room temperature for 10 minutes, and in 0.2× SSC and 0.1% SDS at 55° C. for 30 minutes, after which excess solution was removed; the each filter was exposed to an imaging plate (produced by Fuji Photo Film) for 3 hours and the image was detected using a BAS2000 imaging analyzer (produced by Fuji Photo Film).

As a result, bands hybridizing to the oligonucleotide ACTNH appeared at positions corresponding to about 10 kbp for the BamHI digest, about 2.3 kbp for the PstI digest, and about 450 bp for the SalI digest. Also, bands hybridizing to the oligonucleotide ACTIH appeared at positions corresponding to about 10 kbp for the BamHI digest, about 2.3 kbp for the PstI digest, and about 1 kbp for the SalI digest. For the subsequent experiments, the PstI digest was used, since it is easy to handle.

The genomic DNA digested with restriction enzyme PstI, 20 µg, was subjected to 0.7% agarose gel electrophoresis; a portion corresponding to the band appearing in the above-described hybridization was cut out and subjected to extraction and purification using the EASYTRAP™(produced by Takara Shuzo); the resulting DNA fragment was inserted into the PstI site of pUC19 (produced by Takara Shuzo).

*Escherichia coli* JM109 was transformed with this plasmid, after which it was cultured on 5 round petri dishes 8.5 cm in diameter until 200 to 1,000 colonies per dish were formed. From these plates, 300 colonies were selected and transferred onto a nylon membrane (Hybond-N+, produced by Amersham) placed on a plate of medium. After cultivation at 37° C. for 3 hours, this nylon membrane was kept on filter paper immersed in a solution comprising 0.5 M NaOH and 1.5 M NaCl for 5 minutes (denaturation) and on filter paper immersed in a solution comprising a 0.5 M Tris-HCl buffer (pH 7.0) and 3 M NaCl for 5 minutes (neutralization), followed by rinsing with 2 × SSC. Using this nylon membrane and the oligonucleotide ACTNH (SEQ ID NO:7) as a probe, hybridization was conducted under the same conditions as those described above; three positive colonies were obtained.

These *Escherichia coli* JM109 transformants were designated as P23, P54 and P62, respectively. These transformants were subjected to the alkali lysis method to prepare their plasmid DNAs carrying the clones obtained, which were designated as pACTP23, pACTP54 and pACTP62, respectively. These were analyzed by digestion with several restriction enzymes and gel electrophoresis. As a result, these plasmids were found to share the same insert. With this finding in mind, pACTP54 was used for the experiments that followed.

Digestion of pACTP54 with restriction enzyme SalI yielded an about 1 kbp fragment, about 450 bp fragment, about 300 bp fragment and about 150 bp fragment, which were designated as S1, S2, S3 and S4, respectively. These fragments were subjected to agarose gel electrophoresis, then extracted and purified from the gel, and subcloned into the SalI site of pUC19 (produced by Takara Shuzo); the resulting plasmids were designated as pACTS1, pACTS2, pACTS3 and pACTS4, respectively. These plasmids were further digested with appropriate restriction enzymes (SmaI, BalI, NaeI, etc.) and subjected to self-ligation using a DNA ligation kit (produced by Takara Shuzo) to obtain various deletion variants. The base sequences of these deletion variants and pACTP54 were determined from their end by the dideoxy method.

As a result, it was shown that a sequence encoding the N-terminal amino acid sequence ACTN, a sequence hybridizing with ACTNH (oligonucleotide used as a probe) is present on pACTS2, that a sequence encoding the internal amino acid sequence ACTI, a sequence hybridizing with ACTIH (oligonucleotide used as a probe) is present on pACTS1, and that the four SalI fragments are arranged on pACTP54 in the order of S3, S2, S1 and S4 (FIG. 1).

Translation of these nucleotide sequences into amino acid sequences demonstrated the presence of a signal-like sequence upstream the amino acid sequence of endoglycoceramidase activator II, enabling the deduction of the initiation codon. No stop codon was found downstream this frame; these sequences were found to encode the 417 amino acid residues (SEQ ID NO:9) from the N-terminus of the purified 27.9 kDa trypsin digest of endoglycoceramidase activator II. This 417-residue amino acid sequence corresponds to a molecular weight of 42 kDa. The base sequence encoding this 417-residue amino acid sequence is set forth in SEQ ID NO:10 in the sequence listing. pACTP54 was thus proven to contain the sequence encoding an N-terminal portion of endoglycoceramidase activator II, which includes the 27.9 kDa portion of endoglycoceramidase activator II, the minimum essential unit for its activity.

(4) Cloning of DNA fragment containing the gene encoding C-terminal region of endoglycoceramidase activator II To cover the full-length endoglycoceramidase activator II gene, a DNA fragment encoding the region near the C-terminus, the region which pACTP54 lacks, was screened for by the Southern hybridization method in the same manner as in Example 1 (3). The probe used was the about 0.4 kbp fragment obtained by SmaI/PstI digestion of pACTP54, which contains the DNA sequence nearest to the C-terminus among the sequences obtained in Example 1 (3). Specifically, pACTP54 was digested with restriction enzymes SmaI and PstI (both produced by Takara Shuzo) and subjected to 1% agarose gel electrophoresis; the resulting about 0.4 kbp DNA fragment was cut out.

This DNA fragment was subjected to extraction and purification using the SpinBind™ Series II (produced by Takara Shuzo); the resulting purified DNA fragment was labeled with $^{32}$P using a BcaBEST™ labeling kit (produced by Takara Shuzo). The genomic DNA prepared in Example 1 (1), 50 µg, was digested with restriction enzymes MluI, SacII, ApaI and Eco52I (all produced by Takara Shuzo), each 180 U, at 37° C. for 6 hours. From this reaction mixture, in an amount equivalent to 10 µg of DNA, filters were prepared in the same manner as in Example 1 (3). Each filter was subjected to prehybridization at 68° C. for 3 hours in a solution containing 6 × SSC (1 ×SSC is an aqueous solution of 8.77 g of NaCl and 4.41 g of sodium citrate in 1 l of water), 0.5% SDS, 100 µg/ml herring sperm DNA and 5 × Denhardt's (containing bovine serum albumin, polyvinylpyrrolidone and Ficoll, each at 0.1% concentration), after which the labeled probe was added to a concentration of 0.1 pmol/ml for each, followed by overnight hybridization at 68° C.

Each filter was then washed in 6 × SSC at room temperature for 10 minutes, in 2 × SSC and 0.1% SDS at room temperature for 10 minutes, and in 0.2 × SSC and 0.1% SDS at 70° C. for 30 minutes, after which excess solution was removed; each filter was exposed to an imaging plate (produced by Fuji Photo Film) for 10 minutes and the image was detected using a BAS2000 imaging analyzer (produced by Fuji Photo Film).

As a result, bands hybridizing to the probe appeared at positions corresponding to about 4 kbp for the MluI digest, about 1.3 kbp for the SacII digest, about 1 kbp for the ApaI digest, and about 0.6 kbp for the Eco52I digest. Judging from its size, the Eco52I digest was assumed to fail to completely cover the nearly C-terminal region which pACTPA54 lacks. With this finding in mind, the digests with restriction enzymes MluI, SacII and ApaI were used in the experiments that followed.

The genomic DNA digested with restriction enzyme MluI, SacII or ApaI, 20 µg, was subjected to 0.7% agarose gel electrophoresis; portions corresponding to the bands detected in the above-described hybridization were cut out and subjected to extraction and purification using the EASYTRAP™(produced by Takara Shuzo); the resulting MluI fragment was inserted into the MluI site of pUC19M [plasmid prepared by inserting and ligating a phosphorylated MluI linker (produced by Takara Shuzo) to a digest of pUC19 (produced by Takara Shuzo) with restriction enzyme HincII (produced by Takara Shuzo) to confer an MluI site to pUC19]; the SacII fragment was inserted into the SacII site of pBluescript IISK(−) (produced by Stratagene); and the ApaI fragment was inserted into the ApaI site of pBluescript IISK(−).

*Escherichia coli* HB101 was transformed with these plasmids, after which it was cultured overnight on 10 round petri dishes 8.5 cm in diameter containing an L-agar medium containing 100 µg/ml ampicillin until 200 to 500 colonies per dish were formed. From these dishes, 1,000 colonies were selected and transferred onto a nylon membrane (Hybond-N+, produced by Amersham) placed on a plate of the same medium. After incubation at 37° C. for 10 hours, this nylon membrane was kept on filter paper immersed in a solution comprising 0.5 M NaOH and 1.5 M NaCl for 5 minutes (denaturation) and on filter paper immersed in a solution comprising a 0.5 M Tris-HCl buffer (pH 7.0) and 3 M NaCl for 5 minutes (neutralization), followed by rinsing with 2× SSC. Using this nylon membrane and the about 0.4 kbp DNA fragment obtained by SmaI/PstI digestion of pACTP54 in the same manner as above, hybridization was conducted under the same conditions as those described above. Two positive signals were obtained from colonies containing the ApaI fragment, although no positive signals were obtained from colonies containing the MluI or SacII fragment.

Plasmid DNAs were prepared by the alkali lysis method from the two positive colonies and designated as pBAp42 and pBAp69, respectively. These plasmid DNAs were digested with several restriction enzymes (ApaI, PstI, SalI, Eco52I, BamHI, KpnI, SacI, Eco109I, NaeI, XhoI, SacII, MluI, EcoRI, and HindIII) and analyzed with gel electrophoresis. As a result, pBAp42 and pBAp69 were found to share the same insert. With this finding in mind, pBAp42 was used for the experiments that followed.

pBAp42 was then digested with several restriction enzymes (PstI, SalI, HincII, AccI, and SmaI) and subcloned.

The nucleotide sequences of these subclones and pBAp42 were determined from their end by the dideoxy method, followed by amino acid sequencing using synthetic DNA primers synthesized on the basis of the nucleotide sequences determined. As a result, the same sequence as that of the about 0.4 kbp fragment obtained by SmaI/PstI digestion of pACTP54 was found.

In addition, a 1,740 bp open reading frame (ORF) was found over the region between the PstI fragment in the pACTP54 insert and the ApaI fragment in the pBAp42 insert, whose sequence was determined in Example 1 (3). This ORF was found to begin at the initiation codon ATG and terminate at the stop codon TGA; in the translated amino acid sequence, amino acid sequences corresponding to the amino acid sequences ACTN and ACTI obtained in Example 1 (2) were found.

On the basis of the above results, the entire nucleotide sequence and primary structure of the endoglycoceramidase activator II gene were determined. The results are given in FIG. 1, in which the restriction enzyme maps for the pACTP54 and pBAp42 inserts and the positions of these inserts and the endoglycoceramidase activator II gene are shown.

The nucleotide sequence of the ORF of endoglycoceramidase activator II is set forth in SEQ ID NO:2 in the sequence listing. The entire amino acid sequence of endoglycoceramidase activator II is set forth in SEQ ID NO:1 in the sequence listing.

Example 2

Construction of plasmid for expression of endoglycoceramidase activator II

A plasmid for endoglycoceramidase activator II expression in *Escherichia coli* was constructed by isolating the endoglycoceramidase II structural gene from pACTP54 and pBAp42 as obtained in Example 1, in which the segments of the structural gene are separately present, ligating the gene to a plasmid appropriate for its expression in *Escherichia coli*, and introducing it to an *Escherichia coli* cell.

(1) Construction of plasmid for expression of N-terminal region active polypeptide of endoglycoceramidase activator II pACTP54 as obtained in Example 1 was digested with restriction enzyme SacII and subjected to agarose gel electrophoresis, after which an about 670 bp fragment was extracted and purified using the EASYTRAP™(produced by Takara Shuzo). After terminal blunting using a DNA blunting kit (produced by Takara Shuzo), the fragment was further digested with restriction enzyme MluI and subjected to agarose gel electrophoresis, after which an about 450 bp DNA fragment was extracted and purified to yield a SacII-MluI fragment.

Next, pACTP54 was digested with restriction enzymes EcoRI and MluI and subjected to agarose gel electrophoresis, followed by extraction and purification, to yield an about 820 bp MluI-EcoRI fragment.

Figure 2:
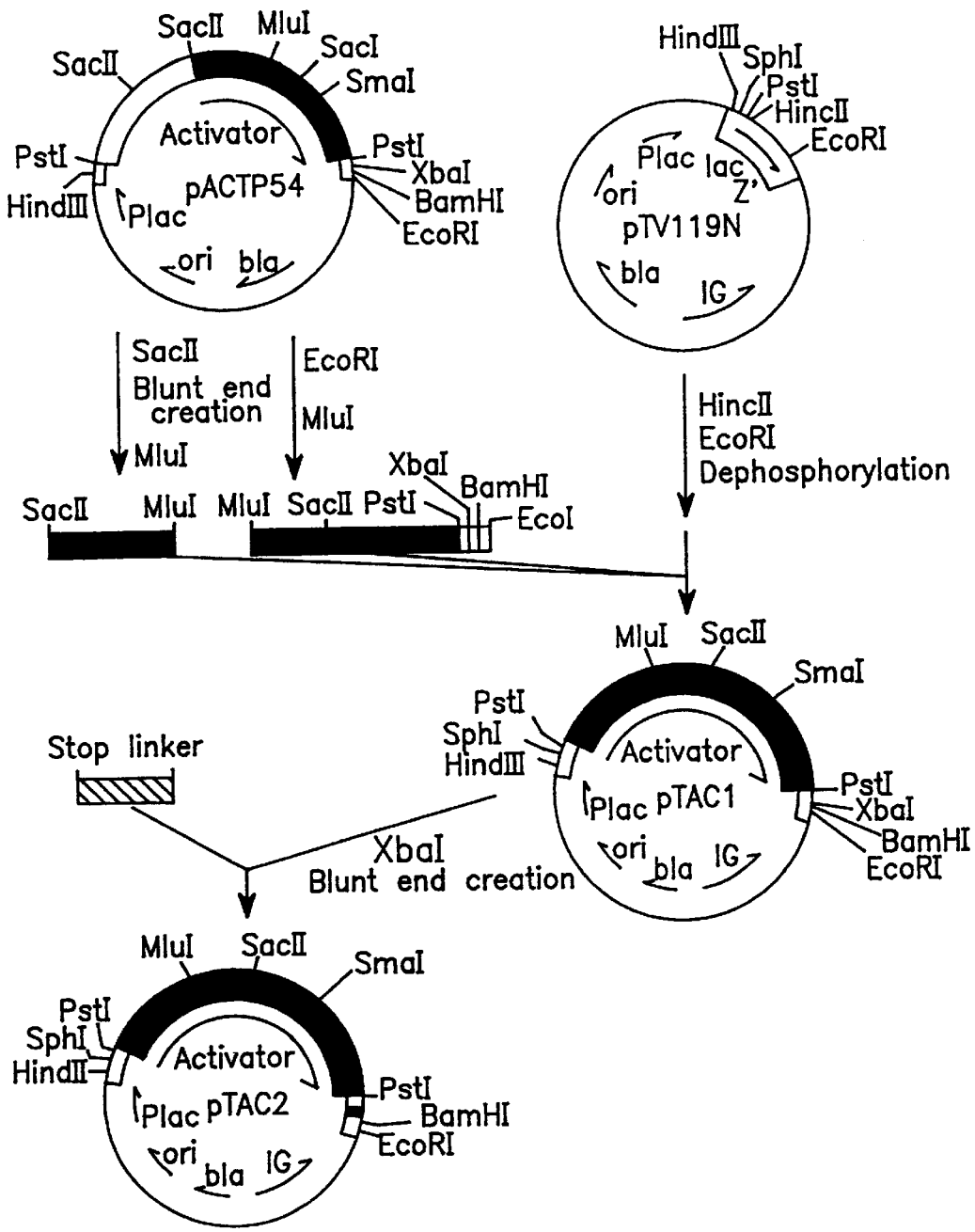
FIG. 2 is a construction diagram of plasmid pTAC2.

These two fragments were inserted into the HincII-EcoRI site of pTV119N (produced by Takara Shuzo) using a DNA ligation kit (produced by Takara Shuzo). The resulting plasmid, designated as pTAC1, was digested with restriction enzyme XbaI, followed by terminal blunting, after which a stop linker (SEQ ID NO:11) was inserted. The resulting plasmid was designated as pTAC2 (FIG. 2).

Figure 3:
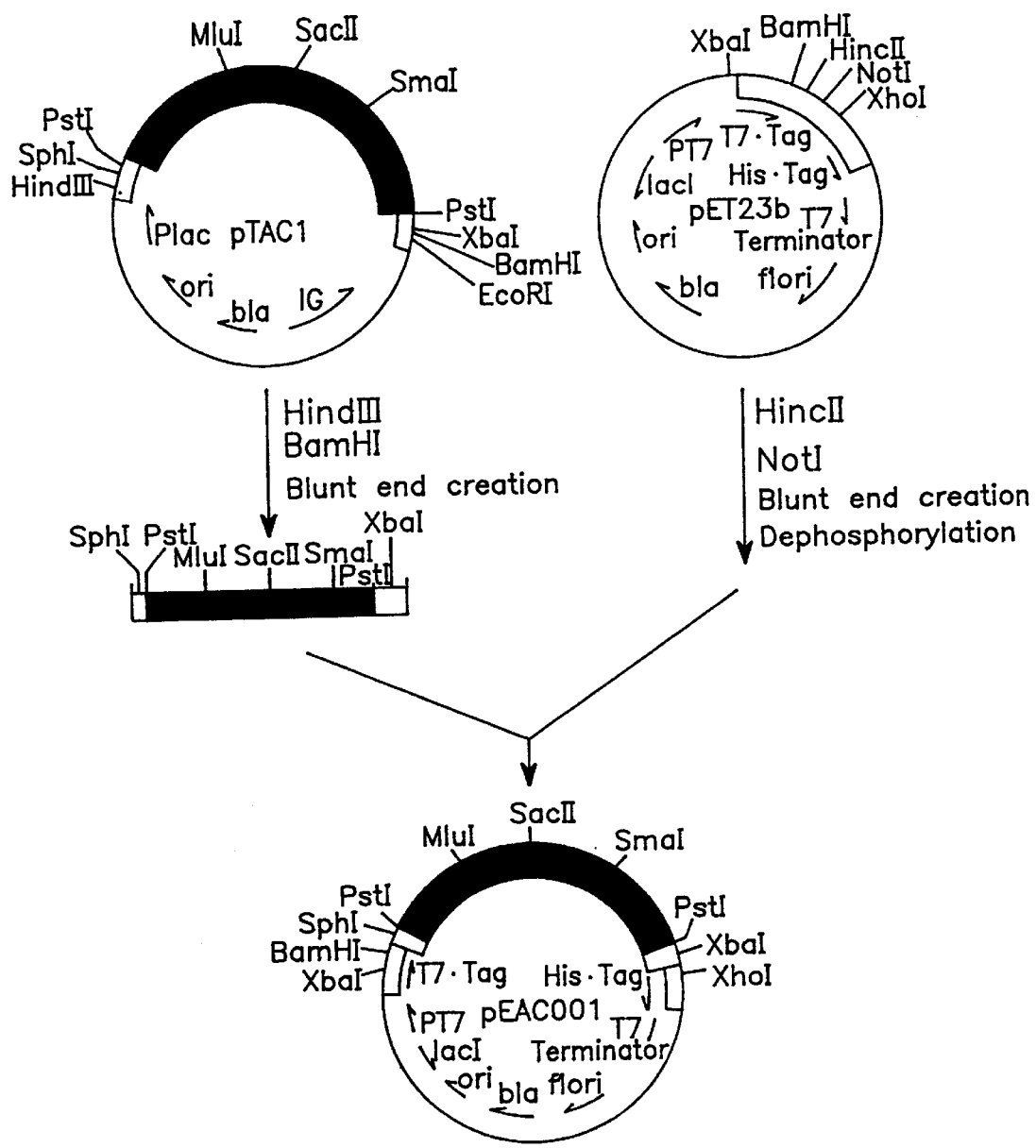
FIG. 3 is a construction diagram of plasmid pEAC001.

Since this pTAC2 contains a sequence encoding 13 amino acid residues, including a laczα-derived peptide, upstream the gene encoding endoglycoceramidase activator II, it is expected that expression of endoglycoceramidase activator II, as a fusion complex with laczα, is induced by use of the SD sequence and initiation codon of lacZ. This pTAC2 was introduced into the *Escherichia coli* JM109 strain; after plasmid DNA was prepared from the resulting recombinant by the alkali lysis method, the base sequence of the insert was identified. The *Escherichia coli* JM109 transformed with pTAC2 was designated as *Escherichia coli* JM109/pTAC2.

pTAC1 was digested with restriction enzymes HindIII and BamHI, followed by terminal blunting and agarose gel electrophoresis, after which an about 1.3 kbp DNA fragment was extracted and purified. The purified fragment was inserted between the HincII site and the blunt-ended NotI site of pET23b (produced by Novagen). This plasmid was designated as pEAC001 (FIG. 3).

Figure 4:
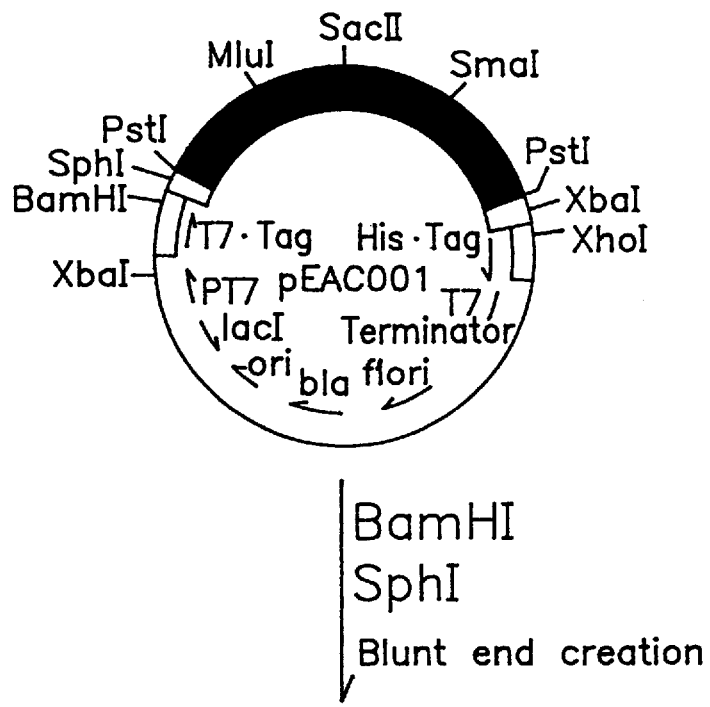
FIG. 4 is a construction diagram of plasmid pEAC101.
Figure 4:
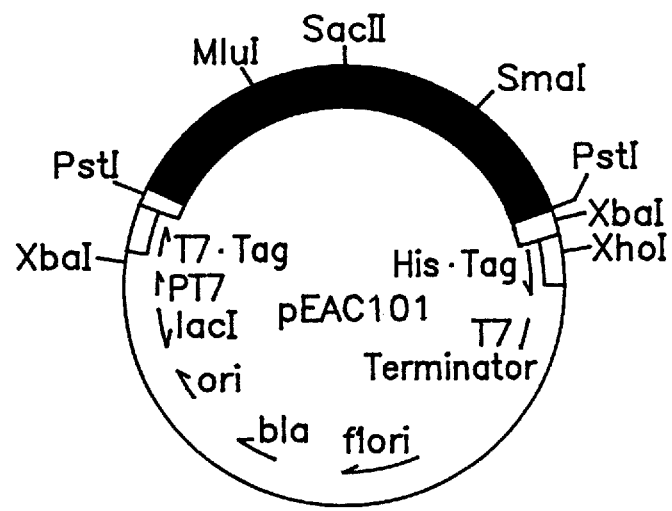

Since this pEAC001 contains the T7 ·Tag™ sequence (encoding amino acid sequence of the first 11 residues of bacteriophage T7 gene 10 protein, produced by Novagen) and a sequence encoding 14 amino acid residues derived from the cloning site, upstream the gene encoding endoglycoceramidase activator II, with the His·Tag™ sequence (sequence encoding 6 histidine residues, produced by Novagen) downstream the endoglycoceramidase activator II gene, it is expected that expression of endoglycoceramidase activator II, as a fusion complex of the N-terminal 417 residues of matured endoglycoceramidase activator II with the T7·Tag™ and His·Tag™ is induced. This plasmid was introduced into the *Escherichia coli* JM109 strain; from the resulting recombinant, plasmid DNA was prepared by the alkali lysis method, after which the nucleotide sequence of the insert was identified. A plasmid proven to have been correctly constructed was introduced to *Escherichia coli* BL21(DE3) for expression. The *Escherichia coli* BL21 (DE3) transformed with pEAC001 was designated as *Escherichia Coli* BL21(DE3)/pEAC 001.

pEAC001 was digested with restriction enzymes BamHI and SphI, followed by terminal blunting and self-ligation. The resulting plasmid was designated as pEAC101 (FIG. 4).

Figure 5:
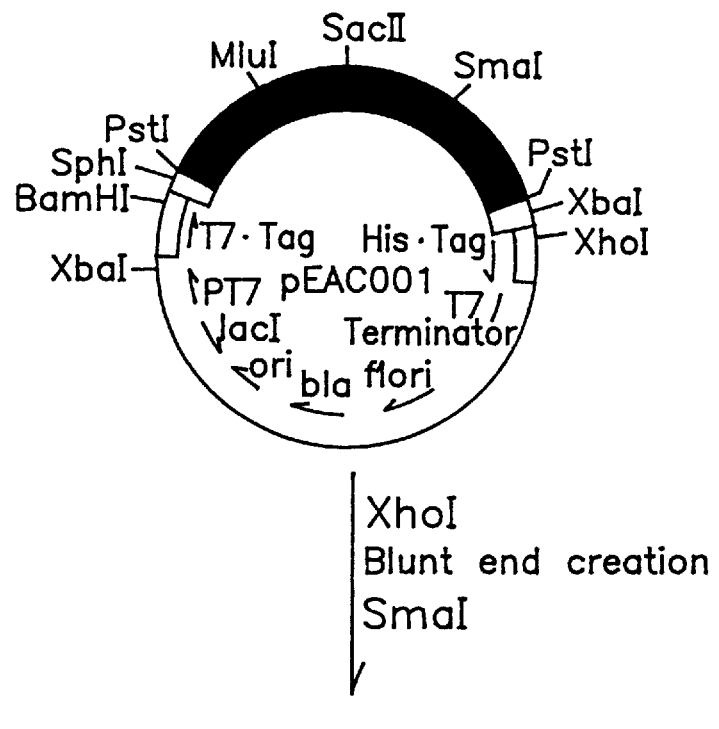
FIG. 5 is a construction diagram of plasmid pEAC002.
Figure 5:
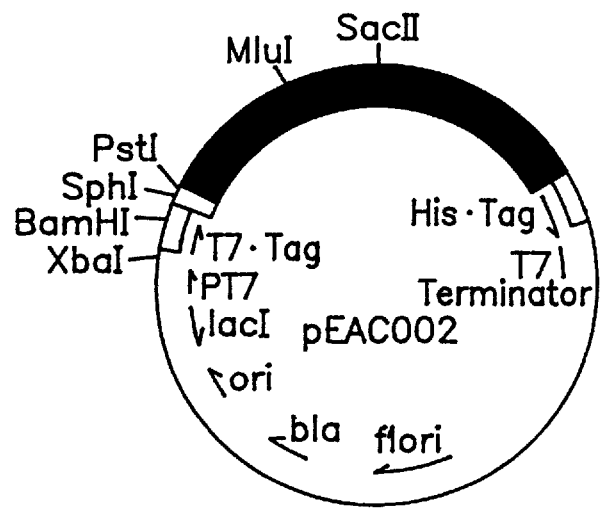

This plasmid is expected to inductively express endoglycoceramidase activator II, as a fusion complex having a fused protein portion shorter than that of pEAC001 by 9 amino acid residues encoded in the sequence derived from the cloning site. This plasmid was introduced to the *Escherichia coli* JM109 strain; from the resulting recombinant, plasmid DNA was prepared by the alkali lysis method, after which the base sequence of the insert was identified. A plasmid proven to have been correctly constructed was introduced into *Escherichia coli* BL21(DE3) for expression. The *Escherichia coli* BL21(DE3) transformed with pEAC101 was designated as *Escherichia coli* BL21(DE3)/pEAC101 [deposited under accession number FERM BP-5531 at the National Institute of Bioscience and Human-Technology, Agency of Industrial Science and Technology; this strain was first deposited under the name of *Escherichia coli* BL2(DE3)/pEAC101 (registration certificate), but the erroneous designation was corrected as above upon issuance of the Microbial Deposit Certificate of Jun. 15, 1995].

pEAC001 was digested with restriction enzyme XhoI, followed by terminal blunting, digestion with SmaI and self-ligation, to yield a plasmid lacking the sequence encoding 143 residues and retaining the sequence encoding 274 N-terminal residues of matured endoglycoceramidase activator II of pEAC001. The resulting plasmid was designated as pEAC002 (FIG. 5). This plasmid was introduced into the *Escherichia coli* JM109 strain; from the resulting recombinant, plasmid DNA was prepared by the alkali lysis method, after which the nucleotide sequence of the insert was identified. A plasmid proven to have been correctly constructed was introduced into *Escherichia coli* BL21 (DE3) for expression. The *Escherichia coli* BL21(DE3) transformed with pEAC002 was designated as *Escherichia coli* BL21(DE3)/pEAC002.

Figure 6:
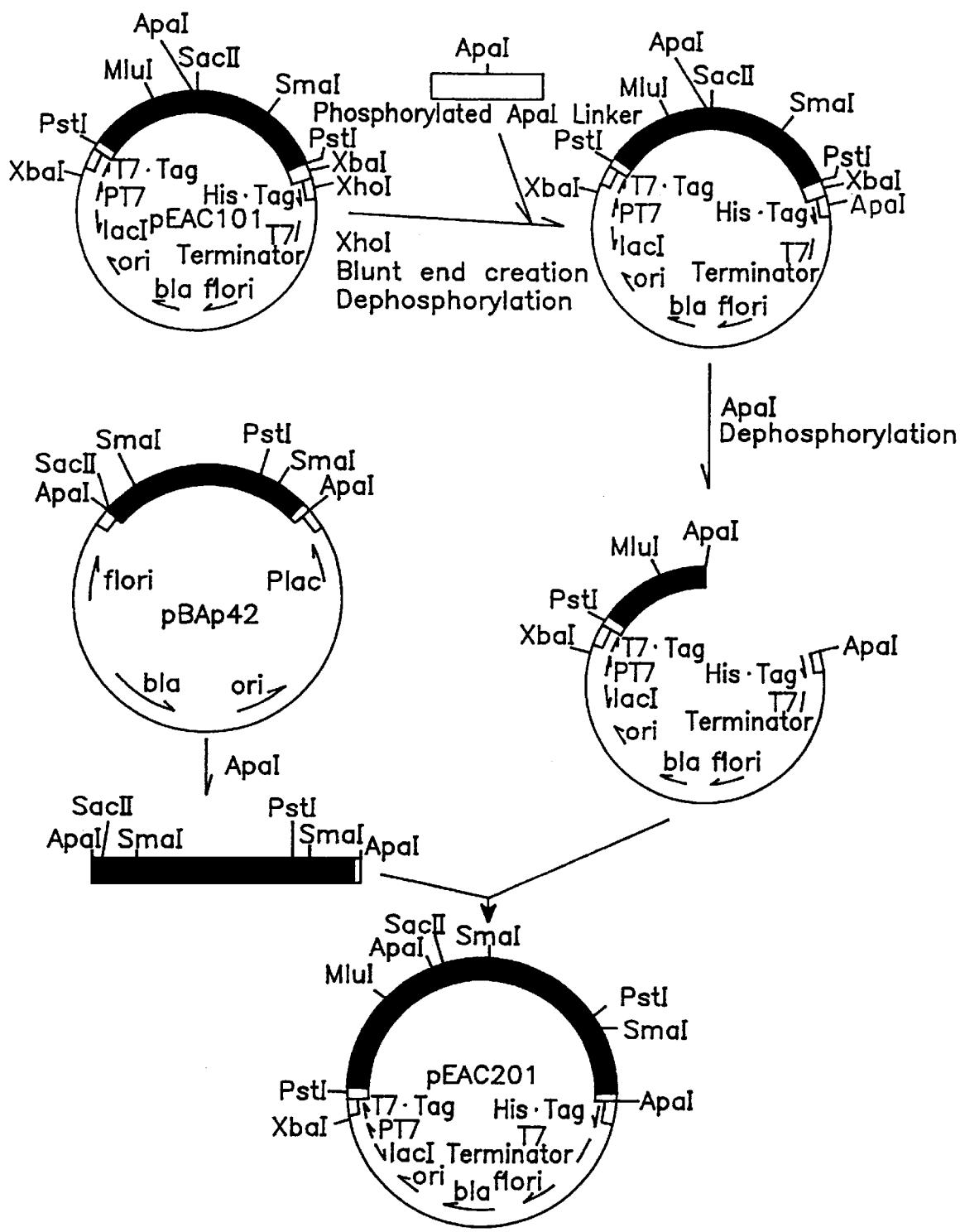
FIG. 6 is a construction diagram of plasmid pEAC201.

(2) Construction of plasmid for expression of endoglycoceramidase activator II polypeptide without signal sequence.

pBAp42 was digested with restriction enzyme ApaI and subjected to agarose gel electrophoresis, followed by extraction and purification from the gel, to yield an about 1,000 bp BAp42-ApaI fragment. Separately, pEAC101 as obtained in Example 2 was digested with restriction enzyme XhoI, followed by terminal blunting using a DNA blunting kit (produced by Takara Shuzo); to this fragment, a phosphorylated ApaI linker (produced by Takara Shuzo) was inserted and ligated, to provide pEAC101 with an ApaI site. This plasmid was digested with restriction enzyme ApaI and dephosphorylated with *Escherichia coli*-derived alkaline phosphatase, followed by ligation of the BAp42-ApaI fragment, to yield pEAC201 (FIG. 6).

This plasmid was introduced into the *Escherichia coli* JM109 strain; from the resulting recombinant, plasmid DNA was prepared by the alkali lysis method, after which the nucleotide sequence of the insert was identified. A plasmid proven to have been correctly constructed was introduced into *Escherichia coli* BL21(DE3) for expression. The *Escherichia coli* BL21(DE3) transformed with pEAC201 was designated as *Escherichia coli* BL21(DE3)/pEAC201.

Example 3

Expression of recombinant endoglycoceramidase activator II in *Escherichia coli*

(1) Expression of polypeptide possessing endoglycoceramidase activator II activity in *Escherichia coli*

*Escherichia coli* JM109/pTAC2, *Escherichia coli* BL21 (DE3)/pEAC001, *Escherichia coli* BL21(DE3)/pEAC101, *Escherichia coli* BL21(DE3)/pEAC002 and *Escherichia coli* BL21(DE3)/pEAC201 as obtained in Example 2 were each inoculated to 5 ml of an L medium containing 100 μl/ml ampicillin, and subjected to overnight shaking culture at 37° C.; 0.2% of the culture broth was further inoculated to 5 ml of the same medium. Upon reach of a turbidity (absorbance at 660 nm) of about 0.5 during cultivation, IPTG was added to a final concentration of 1 mM, followed by shaking culture for 16 hours. After completion of the cultivation, the culture broth was centrifuged; cells were collected, suspended in 0.5 ml of a 20 mM Tris-HCl buffer (pH 7.9), disrupted by ultrasonication, and centrifuged to yield two fractions: an *Escherichia coli* cell extract as the supernatant and a precipitate. The extract and precipitate were subjected to SDS polyacrylamide gel electrophoresis and stained with Coomassie Brilliant Blue.

As a result, endoglycoceramidase activator II was not detected in the case of *Escherichia coli* JM 109/pTAC2. On the other hand, a band attributable to endoglycoceramidase activator II was detected in the extract and precipitate in the case of *Escherichia coli* BL21(DE3)/pEAC001, *Escherichia coli* BL21(DE3)/pEAC101 and *Escherichia coli* BL21 (DE3)/pEAC201, and in the precipitate in the case of *Escherichia Coli* BL21(DE3)/pEAC002; thereby confirming the expression of endoglycoceramidase activator II. *Escherichia Coli* BL21(DE3)/pEAC001 produced the highest concentration of endoglycoceramidase activator II in the soluble fraction. Also, the expression product of *Escherichia coli* BL21(DE3)/pEAC201 provided a band at a position almost the same as that for the native endoglycoceramidase activator II produced by Rhodococcus sp. M-777.

Next, cell extracts from *Escherichia coli* BL21(DE3)/ pEAC001, *Escherichia Coli* BL21(DE3)/pEAC101 and *Escherichia coli* BL21(DE3)/pEAC201 were digested with trypsin by the method described in the Journal of Biochemistry 110, 328–332 (1991). Each digest was subjected to SDS polyacrylamide gel electrophoresis, then electroblotted onto a PVDF membrane. This membrane was subjected to specific immunological staining using an antiserum obtained by immunizing a rat with the 27.9 kDa trypsin digest of purified endoglycoceramidase activator II from Rhodococcus sp. M-777. As a result, an about 28 kDa band attributable to trypsin digest of endoglycoceramidase activator was detected.

This fact suggests that the endoglycoceramidase activator II produced by *Escherichia Coli* BL21(DE3)/pEAC001, *Escherichia coli* BL21(DE3)/pEAC101 and *Escherichia Coli* BL21(DE3)/pEAC201 in their soluble fraction occurs as a mixture of native structure and miss-folded steric structures.

(2) Purification of soluble expression product

*Escherichia coli* BL21(DE3)/pEAC101 was inoculated to 5 ml of an L medium containing 100 μg/ml ampicillin, and subjected to shaking culture at 37° C. for 16 hours; 0.6 ml of the culture broth was further inoculated to 300 ml of the same medium, followed by shaking culture at 37° C. Upon reach of a turbidity (absorbance at 660 nm) of about 0.5 in the culture broth, IPTG was added to a final concentration of 1 mM, followed by overnight shaking culture at 37° C.

After completion of the cultivation, cells were collected via centrifugation, suspended in 10 ml of a 20 mM Tris-HCl buffer (pH 7.9), disrupted by ultrasonication, and centrifuged to separate the supernatant from the precipitate. To the supernatant, 10 ml of a 40 mM Tris-HCl buffer (pH 7.9) containing 10 mM imidazole and 1 M NaCl was added to yield a sample solution.

This sample solution was subjected to affinity chromatography to purify a soluble fraction expression product. Specifically, a column of His·Bind metal chelating resin (produced by Novagen), to which $Ni^{2+}$ was previously immobilized, was equilibrated with a 20 mM Tris-HCl buffer (pH 7.9) containing 5 mM imidazole and 0.5 M NaCl. After the sample solution was added to this column, the column was washed with a 20 mM Tris-HCl buffer (pH 7.9) containing 60 mM imidazole and 0.5 M NaCl, followed by elution with a 20 mM Tris-HCl buffer (pH 7.9) containing 1 M imidazole and 0.5 M NaCl, to yield 10 ml of a purified soluble expression product.

(3) Refolding and production of recombinant 27.9 kDa endoglycoceramidase activator II Ten milliliters of the purified soluble expression product from *Escherichia coli* BL21(DE3)/pEAC101 obtained in Example 3 (2) was added drop by drop to 990 ml of a 20 mM Tris-HCl buffer (pH 7.9) with stirring; the resulting dilution was stirred at 5° C. for 4 days to achieve refolding.

This solution was added to a His·Bind metal chelating resin column, followed by washing and elution in the same manner as above to achieve concentration. The buffer for this eluate was replaced with a 25 mM Tris-HCl buffer (pH 8.0) containing 2 mM $CaCl_2$ using a Hi-Trap desalting column (produced by Pharmacia). After digestion with 2 mg of trypsin at 37° C. for 4 hours, additional 2 mg of trypsin was added, followed by digestion at 37° C. for 16 hours, to achieve conversion to the 27.9 kDa endoglycoceramidase activator II. The digest was passed through an anion exchange resin Q cartridge (produced by Bio-Rad), previously equilibrated with a 50 mM Tris-HCl buffer (pH 7.9), and further passed through an affinity column Protrap™ (produced by Takara Shuzo) to remove the trypsin, followed by ultrafiltration to obtain 45 μl of a concentrate.

Analysis by SDS polyacrylamide gel electrophoresis revealed a single band corresponding to a molecular weight of about 28,000. Quantitative determination using the BCA™ protein assay reagent (produced by Pierce) demonstrated a protein content of 11 μg/pl using bovine serum albumin as standard.

Endoglycoceramidase II activating activity was determined by the method described in the Journal of Biochemistry 110, 328–332 (1991); endoglycoceramidase II activating activity was confirmed. In other words, it was proven that about 1.7 mg of the recombinant 27.9 kDa endoglycoceramidase activator II is obtained from 1 liter of the culture broth of *Escherichia coli* BL21(DE3)/pEAC101, which includes the gene of the present invention. The amino acid sequence of this 27.9 kDa endoglycoceramidase activator II is set forth in SEQ ID NO:3 in the sequence listing, and its base sequence is set forth in SEQ ID NO:4 in the sequence listing.

Other modifications of the above described embodiments of the invention which are obvious to those skilled in the art are intended to be within the scope of the following claims.

What is claimed is:

1. An isolated DNA having a sequence encoding a polypeptide possessing endoglycoceramidase activator activity wherein said isolated DNA comprises a DNA sequence selected from the group consisting of:

(a) a DNA sequence of SEQ ID NO:2 or SEQ ID NO:4,
(b) a DNA sequence encoding an amino acid sequence of SEQ ID NO:1 or SEQ ID NO:3; and
(c) a DNA sequence which hybridizes (a) or (b) above.

2. The isolated DNA according to claim 1, wherein the polypeptide is derived from a strain of the genus Rhodococcus.

3. The isolated DNA according to claim 2, wherein the polypeptide is derived from Rhodococcus sp. M-777.

4. A recombinant DNA which comprises the isolated DNA of claim 1.

5. A vector which comprises the recombinant DNA of claim 4.

6. The vector according to claim 5, wherein the recombinant DNA is operably linked to a promoter.

7. A cell of a procaryote or eucaryote transformed with the vector of claim 5.

8. A method for producing a polypeptide possessing endoglycoceramidase activator activity, comprising the steps of:

(a) culturing the cell of claim 7; and (b) recovering the polypeptide possessing endoglycoceramidase activator activity from the culture obtained in Step (a).

9. A synthetic oligonucleotide probe or primer which specifically hybridizes with the isolated DNA of claim 1.

* * * * *